United States Patent [19]

Varshavsky et al.

[11] Patent Number: 5,122,463
[45] Date of Patent: Jun. 16, 1992

[54] METHODS FOR TRANS-DESTABILIZATION OF SPECIFIC PROTEINS IN VIVO AND DNA MOLECULES USEFUL THEREFOR

[75] Inventors: Alexander J. Varshavsky, Boston; Erica S. Johnson, Somerville; David K. Gonda, Quincy; Mark Hochstrasser, Somerville, all of Mass.

[73] Assignee: Massachusetts Institute of Technology, Cambridge, Mass.

[21] Appl. No.: 525,150

[22] Filed: May 17, 1990

[51] Int. Cl.⁵ .................. C12N 15/09; C12N 15/62
[52] U.S. Cl. .................. 435/172.3; 435/69.7; 536/27
[58] Field of Search .......... 435/69.7, 188, 183, 435/172.3; 935/47; 530/402; 536/27

[56] References Cited

FOREIGN PATENT DOCUMENTS

87/02522  4/1988  PCT Int'l Appl. .
89/02651  6/1989  PCT Int'l Appl. .

OTHER PUBLICATIONS

P.N.A.S. vol. 86:2540-2544, Apr. 1989, Butt et al. Ubiquitin fusion augments the yield of cloned gene products, in *Eschlerichia coli*.
K. Nagai and H. C. Thogersen, *Nature* 309:810-812 (1984).
Hershko et al., *Proc. Natl. Acad. Sci. USA* 81:7021-7025 (1985).
Tsunasawa et al., *J. Biol. Chem.* 260:5382-5391 (1985).
Boissel et al., *Proc. Natl. Acad. Sci. USA* 82:8448-8452 (1985).
Thornton et al., *J. Mol. Biol.* 167:443-460 (1983).
Ferber et al., *J. Biol. Chem.* 261:3128-3134 (1986).
Bachmair et al., *Science* 234:179-186 (1986).
Ferber et al., *Nature* 326:808-811 (1988).
Reiss et al., *J. Biol. Chem.* 263:2693-2698 (1988).
Townsend et al., *J. Exp. Med.* 168:1211-1224 (1988).
Bachmair and Varshavsky, *Cell* 56:1019-1032 (1989).
Chau et al., *Science* 243:1576-1583 (1989).
Gonda et al., *J. Biol. Chem.* 264:16700-16712 (1989).
Miller et al., *Biotechnology* 1:698-704 (1989).
Hall and Frieden, *Proc. Natl. Acad. Sci. USA* 86:3060-3064 (1989).

*Primary Examiner*—David L. Lacey
*Assistant Examiner*—John D. Ulm
*Attorney, Agent, or Firm*—Hamilton, Brook, Smith & Reynolds

[57] ABSTRACT

This invention pertains to a method of metabolically destabilizing a protein or peptide of interest in vivo provided that the protein or peptide contains a second determinant of the N-end rule-based degradation signal and provided that another (targeting) protein or peptide can be identified that specifically interacts with the protein or peptide of interest. The methods of the invention comprise contacting the protein or peptide of interest with the targeting protein or peptide which contains a destabilizing amino-terminal amino acid according to the N-end rule of protein degradation but lacking a second determinant of the N-end rule-based degradation signal. Because nearly all proteins specifically interact with other proteins, this is a broadly applicable method for metabolically destabilizing a protein or peptide of interest in vivo.

6 Claims, 22 Drawing Sheets

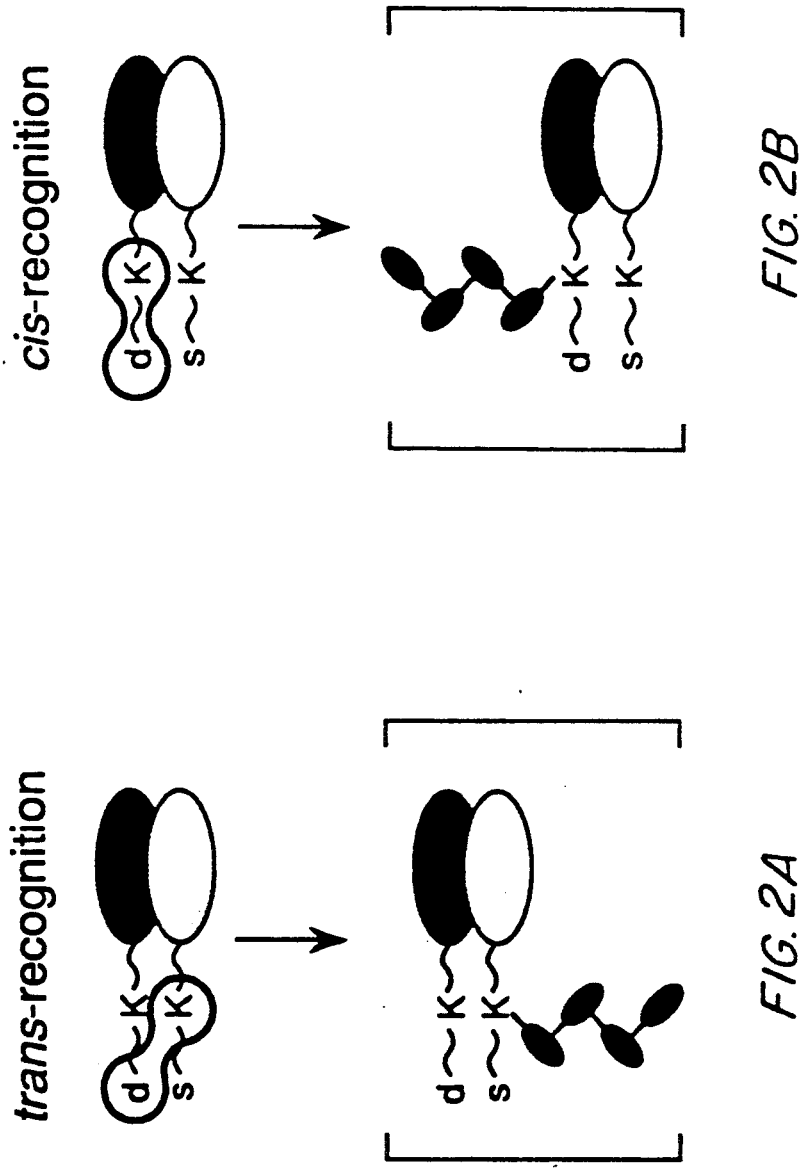

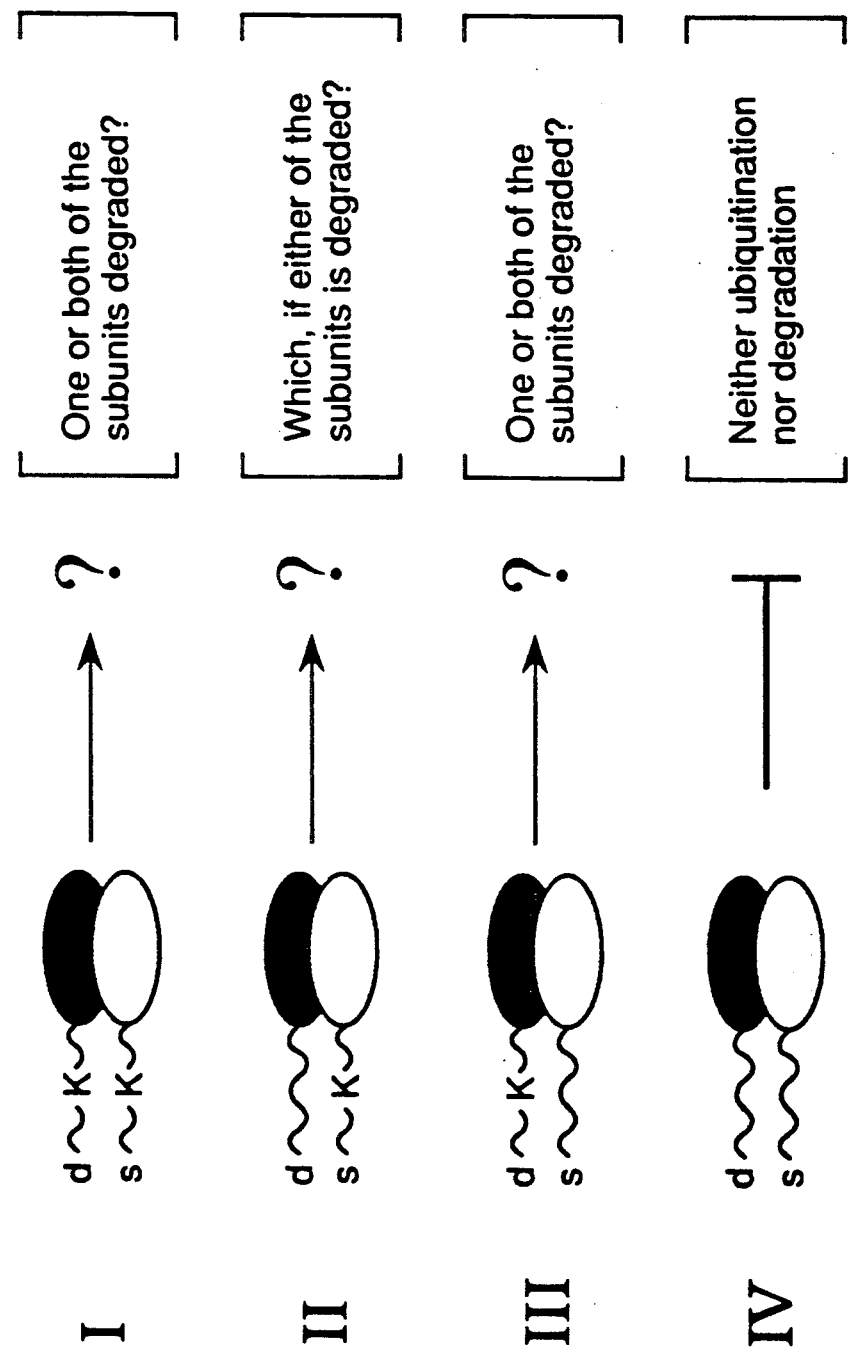

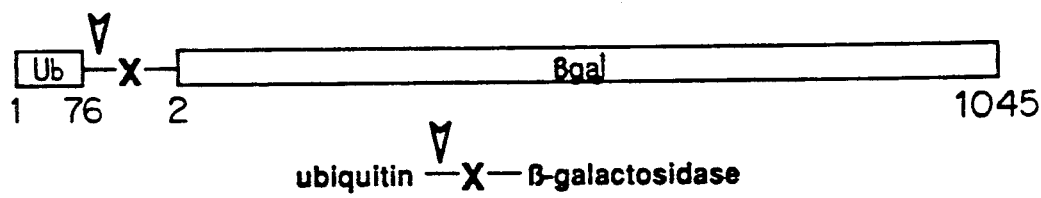
FIG. 3A
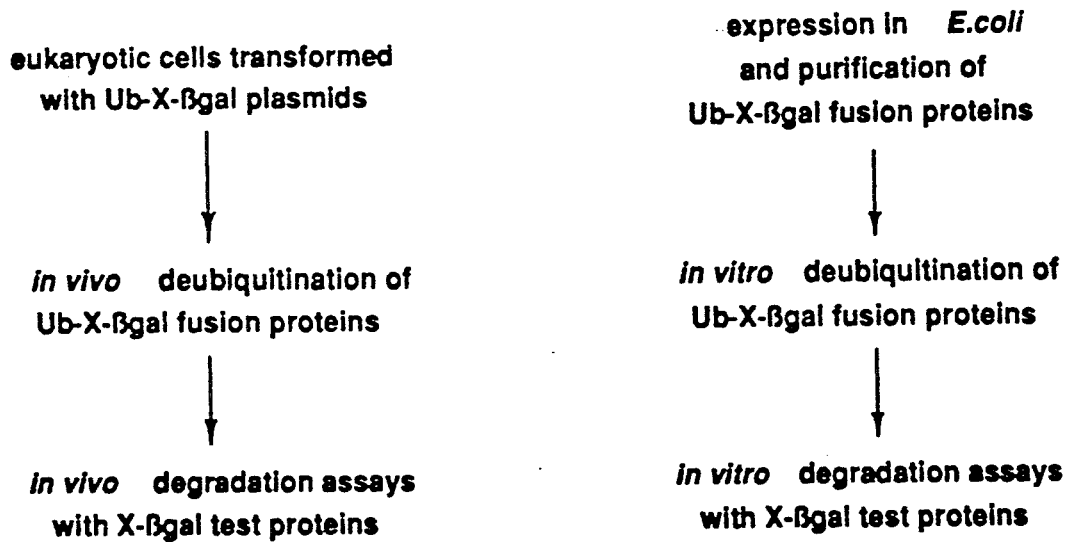
FIG. 3B                    FIG. 3C

```
1  MNKIPIKDLLNPQITDEFKSSILDINKKLFSICCNLPKLPESVTTEEEVELRDILVFLSRANKNRKISDE  67
   EKKLLQTTSQLTTTITVLLKEMRSIENDRSNYQLTQKNKSADGLVFNVVTQDMINKSTKPYRGHRFTKEN  136
   VRILESWFAKNIENPYLDTKGLENLMKNTSLSRIQIKNWVSNRRRKEKTITIAPELADLLSGEPLAKKKE  210
```

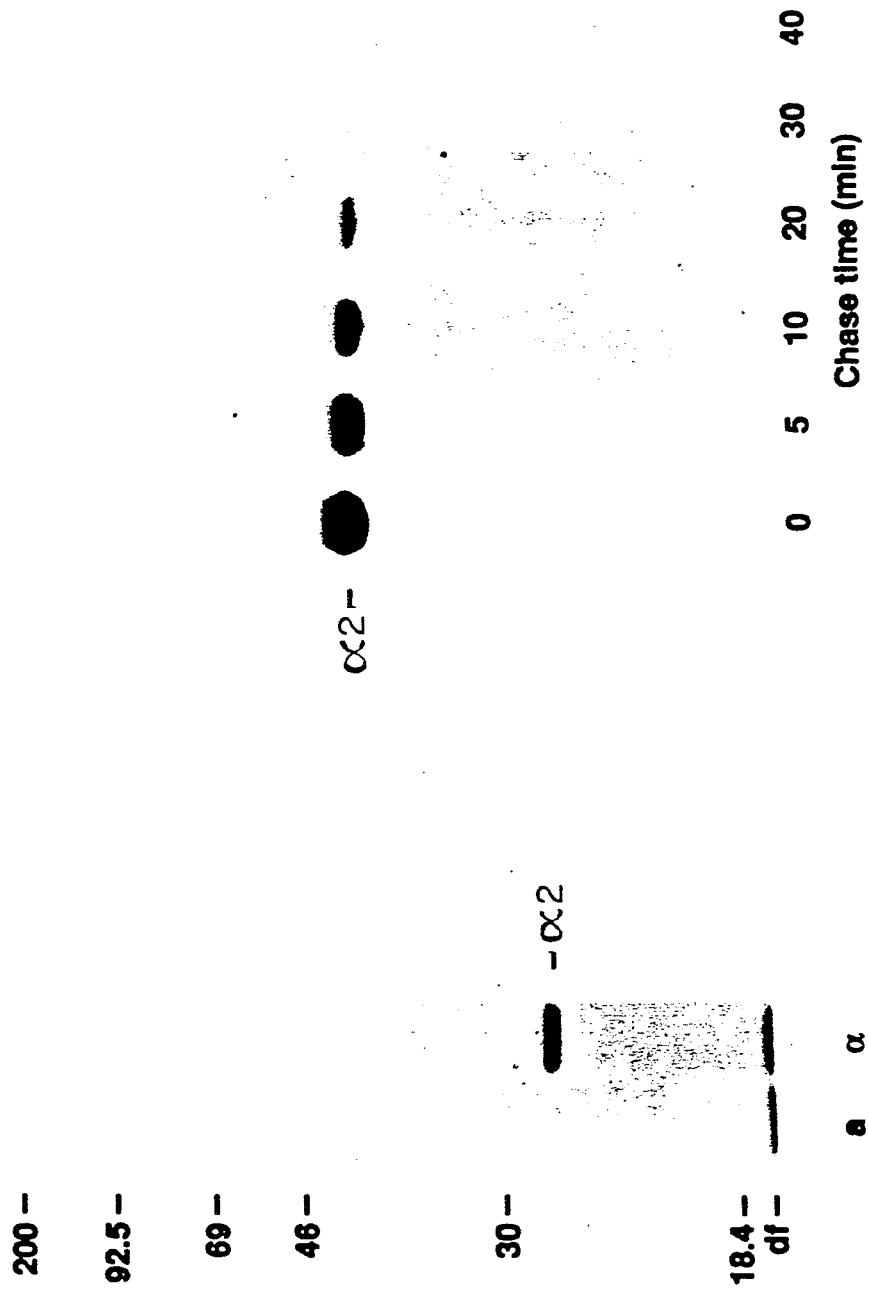

Short-lived β-gal fusion;
colonies white on X-Gal
↓
Mutagenize
↓
Screen for blue colonies
↓
Characterize mutants

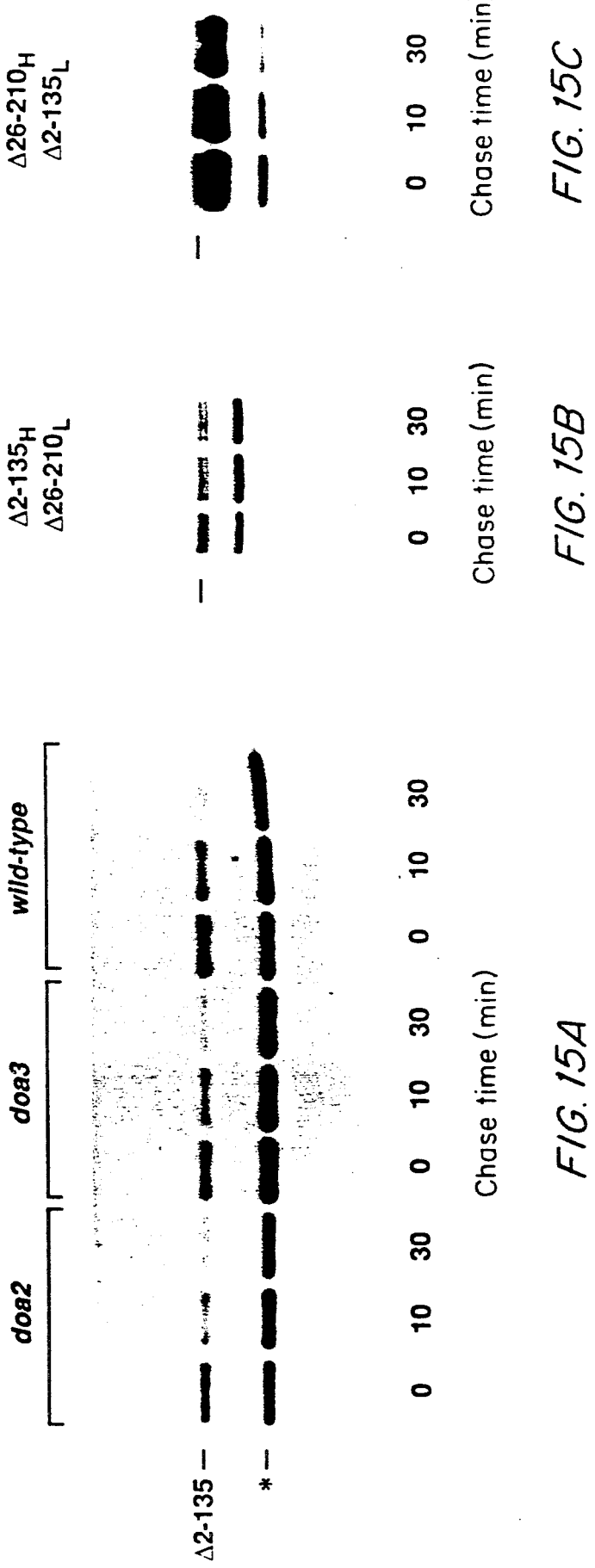

METHODS FOR TRANS-DESTABILIZATION OF SPECIFIC PROTEINS IN VIVO AND DNA MOLECULES USEFUL THEREFOR

GOVERNMENT SUPPORT

This work was supported by the following grants from the National Institutes of Health: GM31530 and DK39520.

BACKGROUND OF THE INVENTION

Ubiquitin, a 76-residue protein, is present in eukaryotes either free or covalently joined, through its carboxyl-terminal glycine residue, to various cytoplasmic, nuclear, and integral membrane proteins. The coupling of ubiquitin to such proteins is catalyzed by a family of ubiquitin-conjugating enzymes (also called E2 enzymes). The fact that the amino acid sequence of ubiquitin is conserved among eukaryotes to an extent unparalleled among known proteins suggested that ubiquitin mediates a basic cellular function. However, the biological role of ubiquitin remained a mystery until relatively recently.

Ubiquitin has been found to be one of several factors required for ATP-dependent protein degradation in eukaryotic cells. One function of intracellular protein degradation, most of which is ATP-dependent, is selective elimination of damaged and otherwise abnormal proteins. Another is to confer short half-lives on undamaged proteins whose concentrations in the cell must vary as functions of time, as is the case, for example, with many regulatory proteins. Many other proteins, while long-lived as components of larger macromolecular complexes such as ribosomes and oligomeric proteins, are metabolically unstable in a free, unassociated state. (The term "metabolic instability" implies a relatively short half-life of a protein as a physical entity in vivo, with the adjective "metabolic" being used to distinguish this property from "stability" as such, which often means either conformational or chemical stability of a protein, but not its existence as a physical entity in vivo.)

Recent work has shown that selective degradation of many short-lived proteins requires a preliminary step of ubiquitin conjugation to a targeted proteolytic substrate. It was proposed that one role of ubiquitin is to serve as a signal for attack by proteases specific for ubiquitin-protein conjugates (reviewed by Finley and Varshavsky, *Trends Biochem. Sci.* 10:343-348 (1985)).

This understanding, however, left unsolved the problem of targeting: how are intracellular proteins initially recognized as proteolytic substrates? At least some short-lived proteins are recognized as such because they contain sequences (degradation signals) which make these proteins substrates of specific proteolytic pathways. The first degradation signal to be understood in some detail comprises two distinct determinants: the protein's amino-terminal residue and a specific internal lysine residue (Bachmair et al., *Science* 234:179-186 (1986); Bachmair and Varshavsky, *Cell* 56:1013-1032 (1989)). The N-end rule a code that relates the protein's metabolic stability to the identity of its amino-terminal residue (Bachmair et al., *Science* 234:179-186 (1986)), is universal in that different versions of the N-end rule operate in all of the eukaryotic organisms examined, from yeast to mammals (Gonda et al., *J. Biol. Chem.* 264:16700-16712 (1989)).

The second essential determinant of the N-end rule-based degradation signal, referred to herein as the second determinant, is a specific internal lysine residue in the substrate protein that serves as the site of attachment of a multiubiquitin chain. Formation of the multiubiquitin chain on a targeted short-lived protein is essential for the protein's subsequent degradation (FIG. 1). The enzymatic conjugation of ubiquitin to other proteins involves formation of an isopeptide bond between the carboxy-terminal glycine residue of ubiquitin and the ε-amino group of a lysine residue in an acceptor protein. In a multiubiquitin chain, ubiquitin itself serves as an acceptor, with several ubiquitin moieties attached sequentially to an initial acceptor protein to form a chain of branched ubiquitin-ubiquitin conjugates (Chau et al., *Science* 243:1576-1583 (1989)).

The elucidation of the fundamental rules governing the metabolic stability of proteins in cells, and especially the deciphering of the N-end rule-based degradation signal, has made possible the manipulation of proteins to vary their half-lives in vivo (Bachmair and Varshavsky, *Cell* 56:1019-1032 (1989)). A more detailed understanding of these degradation signals, their components, and their interrelationships is necessary in order to realize the full potential of this powerful methodology.

SUMMARY OF THE INVENTION

This invention pertains to methods and compositions for metabolically destabilizing a protein or peptide of interest (i.e., targeting a protein or peptide for degradation). The protein or peptide of interest must contain a second determinant of the N-end rule-based degradation signal. The method comprises contacting the protein or peptide of interest with a targeting protein or peptide which interacts specifically with the protein or peptide of interest. The targeting peptide or protein is characterized as having a destabilized amino-terminal amino acid according to the N-end rule of protein degradation, but lacking a second determinant of the N-end rule-based degradation signal.

In a preferred embodiment, the protein or peptide of interest and the targeting peptide or protein are subunits or portions of subunits of the same oligomeric protein in a living cell. The cell is transformed with an expressible DNA construct encoding a targeting peptide or protein having a destabilizing amino-terminal amino acid according to the N-end rule of protein degradation, but lacking a second determinant of the N-end rule-based degradation signal.

One method for generating a targeting peptide or protein having a destabilizing amino-terminal amino acid residue is to transform a eukaryotic cell with an expressible DNA construct comprising ubiquitin fused in frame to a DNA sequence encoding a peptide or protein which interacts specifically with the protein or peptide of interest.

The methods described herein facilitate the metabolic destabilization of a protein or peptide of interest. A requirement of the method is that it is necessary to identify a peptide or protein which interacts specifically with the protein or peptide of interest. Because nearly all proteins specifically interact with other proteins, this is a broadly applicable method for metabolically destabilizing a protein or polypeptide of interest.

BRIEF DESCRIPTION OF THE FIGURES

FIGS. 2A to B are diagrams illustrating the cis and trans recognition in the N-end rule pathway.

FIGS. 3A to C are diagrams illustrating the use of ubiquitin-protein fusions, exemplified by Ub-X-$\beta$gal, to generate test proteins bearing predetermined amino-terminal residues.

FIGS. 12A to C are diagrams illustrating that the $\alpha$2 repressor is short-lived in vivo.

FIGS. 15A to C are diagrams illustrating that two degradation signals in $\alpha$2 are targeted by different pathways.

DETAILED DESCRIPTION OF THE INVENTION

The invention disclosed in this application relates to a new class of methods for manipulating metabolic stability of a protein or polypeptide of interest. The terms "protein", "polypeptide" and "peptide" are often used interchangeably in the art, with "peptides" sometimes, but not always, referring to relatively short polypeptides, on the order of ~50 residues or less. As used herein, the term protein is meant to encompass both proteins and polypeptides, whereas the term peptide is meant to encompass relatively short polypeptides. As discussed below, a common feature of these methodologies is the use of trans recognition, described in the present patent application, to destabilize metabolically long-lived proteins by targeting them for selective degradation in trans.

In a monomeric protein substrate, both determinants of the degradation signal are located, by definition, within the same polypeptide chain (cis recognition). However, in the case of a multisubunit protein substrate, it is conceivable that the first and second determinants of the signal might residue within different subunits of the substrate (trans recognition). A question which could be addressed is whether the targeting and degradation components of a proteolytic pathway distinguish between the subunits of an oligomeric protein that carry the degradation signals from those that do not, or whether the entire oligomeric protein is targeted for destruction even if only some of its subunits carry degradation signals. If either trans recognition of proteolytic substrates or their subunit-specific degradation, or both were possible (FIGS. 2A to C), this would have important functional and practical implications.

Figure 1:
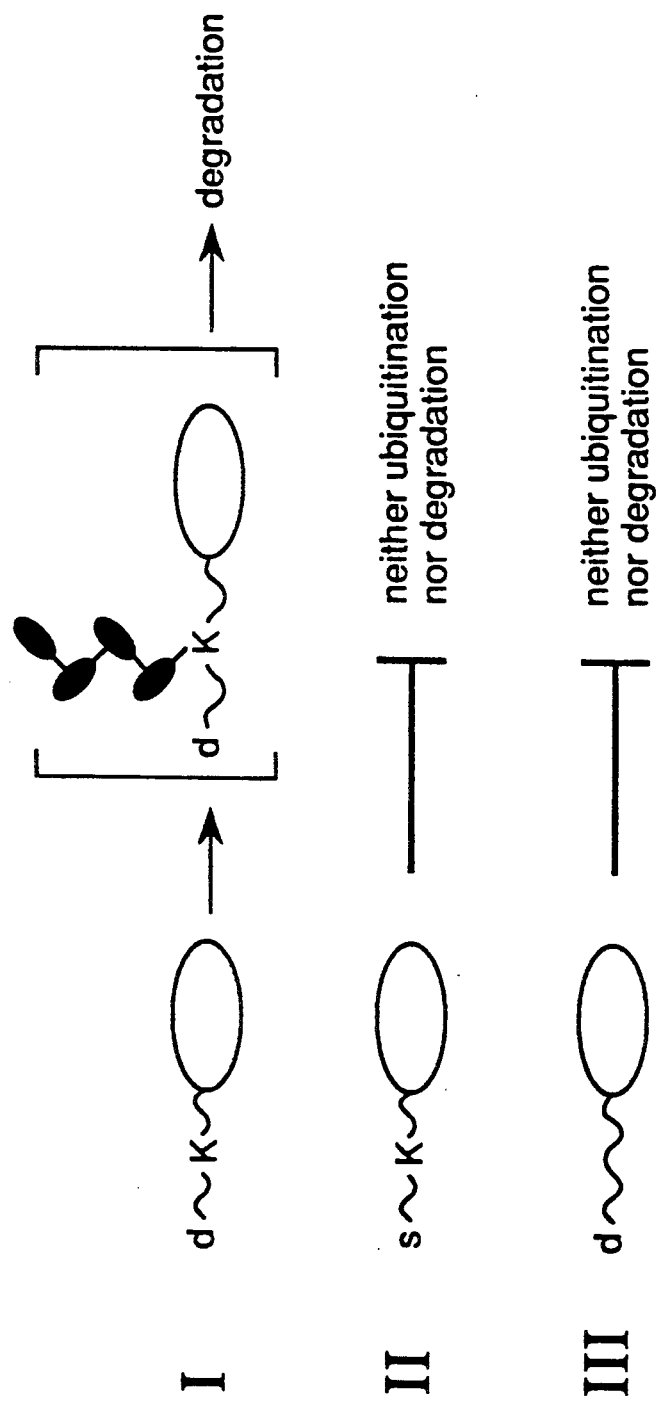
FIG. 1 is a diagram showing the two-determinant organization of the N-end rule-based degradation signal in a monomeric protein, with d and s denoting, respectively, a destabilizing and a stabilizing amino-terminal residue, and the chain of black ovals joined to the second-determinant lysine (K) denoting a multiubiquitin chain.

The N-end rule proteolytic pathway has been the subject of numerous scientific articles over the past several years. These studies have shown that the N-end rule-based degradation signal is composed of two distinct determinants: the protein's amino-terminal residue and a specific internal lysine residue (FIG. 1).

The first determinant, reported initially by Bachmair et al. (*Science* 234:179-186 (1986)), is the amino-terminal amino acid residue of the protein (shown in FIG. 1 as "d" for destabilizing or "s" for stabilizing). The initial report by Bachmair et al. describes an assay used to study the effect of the amino-terminal residue on metabolic stability of a test protein. In the yeast *S. cervisiae* it was determined that the group of destabilizing amino-terminal residues consisted of Ile, Glu, His, Tyr, Gln, Phe, Leu, Asp, Asn, Lys, Arg and Trp. Subsequent work by Gonda et al. (*J. Biol. Chem.* 264:16700-16712 (1989) served to elucidate the set of destabilizing residues in mammalian reticulocytes. This set consisted of Asn, Gln, Asp, Glu, Cys, Arg, Lys, His, Phe, Leu, Trp, Tyr, Ala, Ser and Thr. As described below, the assays which were used to determine the destabilizing residues in these two systems can be readily and directly adapted to make an analogous determination in any eukaryotic system.

In all eukaryotes examined, ubiquitin-X-$\beta$gal (Ub-X-$\beta$gal) fusion proteins are precisely deubiquitinated either in vivo or in cell-free extracts by an endogenous processing protease to yield X-$\beta$gal test proteins bearing the (predetermined) residue X at the amino terminus (FIGS. 3A to C) (Bachmair et al., *Science* 234:179-186 (1986)). Depending on the nature of X, the X-$\beta$gal proteins are either long-lived or metabolically unstable, with destabilizing amino-terminal residues conferring short half-lives on the corresponding X-$\beta$gals. This amino-terminal degradation signal is manifested as the N-end rule.

It has previously been found that the exact form of the N-end rule varies between different types of cells. The methods for determining the exact form of the N-end rule in any given cell type are technically straightforward, and involve expressing, in a cell type of interest, using standard expression vectors, a set of Ub-X-$\beta$gal fusion proteins described above and determining, using standard pulse-chase protocols and immunoprecipitation, the half-lives of each of the 20 different X-$\beta$gal proteins. Specifically, an X-$\beta$gal protein (derived from a Ub-X-$\beta$gal by deubiquitination) is pulse-labeled in vivo with a radioactive amino acid, followed by a cold chase, using which the metabolic fate of the pulse-labeled species is determined. The way to implement this latter portion of the protocol is also well known to those skilled in the art, and consists of immunoprecipitation of each of the X-$\beta$gal proteins from pulse-labeled and chased samples of the corresponding crude extracts using an antibody to $\beta$gal, followed by electrophoretic analysis of immunoprecipitated X-$\beta$gals, which completes this direct determination of the N-end rule in a cell type of interest (Bachmair et al., Science 234:179-186 (1986); Bachmair and Varshavsky, Cell 56:1019-1032 (1989)).

While the first determinant of the N-end rule-based degradation signal is the protein's amino-terminal residue, the second, also essential, determinant of this signal is a specific internal lysine residue in the same protein (shown as "K" in FIG. 1). The available evidence indicates that the relevant features of the second-determinant lysine are its spatial (but not necessarily "linear") proximity to the protein's amino-terminal residue and segmental mobility of the lysine-containing region. In a stochastic view of the second determinant, each lysine of a proteolytic substrate can be assigned a probability of being utilized as a ubiquitination site, depending on the time-average spatial location and mobility of the lysine. For most or all of the lysine residues in a given protein, the probability of serving as a multiubiquitination site would be either small or infinitesimal because of their spatial remoteness from the protein's amino-terminal residue, lack of mobility or both (Bachmair and Varshavsky, Cell 56:1013-1032 (1989)).

While the understanding, in precise physio-chemical terms, of what exactly makes a lysine residue in a protein a second determinant (ubiquitination site) of the N-end rule-based degradation signal is not yet complete, the procedure for determining, in each specific case, whether a given protein or polypeptide of interest has an efficient second determinant is both well defined and technically straightforward. Indeed, to determine whether a given protein of interest has an efficient multiubiquitination site (the second determinant of the N-end rule-based degradation signal), it is sufficient to determine, whether the in vivo half-life of this protein is a function of its amino-terminal residue. Since the presence of both the first and the second determinant is essential for the function of the N-end rule-based degradation signal, one could directly determine whether the second determinant is present in a protein of interest by asking whether the in vivo half-life of this protein is short when its amino-terminal residue is destabilizing according to the N-end rule. In other words, if a protein's metabolic stability is a strong function of its amino-terminal residue (as is the case for instance, with X-$\beta$gals, where Arg-$\beta$gal is ~500-fold shorter-lived than Val-$\beta$gal), this protein, by definition, has an efficient second determinant of the N-end rule-based degradation signal. Either the absence of or a weak dependence of a protein's half-life on the identity of its amino-terminal residue define this protein as lacking an efficient second determinant.

The information about exactly where the second determinant-lysine (the multiubiquitination site) is located within a protein or peptide of interest can be obtained by direct chemical mapping (Chau et al., Science 243:1576-1583 (1989)) or other means. However, this additional information is in most cases unnecessary for the purposes of the present invention.

Selective destruction of long-lived proteins that is made possible by the methodology of the present invention could be viewed, in a larger context, as a new way to generate specific null phenotypes. Producing null or nearly null phenotypes of specific genes is a recurring theme in both basic and applied biological research. The underlying goals range from suppressing the functions of toxic and otherwise undesirable proteins, such as those of pathogenic viruses or aberrant proto-oncogene products, to analyzing the function of a protein of interest by selectively eliminating the function and observing the effects of such an elimination. Deletions of predetermined genes directly yield the desired null phenotypes. Such targeted deletions are technically straightforward for some single-cell organisms such as bacteria and yeast, but are either difficult or impossible, at present, with most animals and plants.

Alternative approaches to producing null or nearly null phenotypes of specific genes include "conventional" pharmacology, e.g., the use of inhibitors of specific enzymes. For instance, penicillin, by specifically inhibiting one of the enzymes required for the synthesis of bacterial wall, generates, in effect, a (partially) null phenotype of the gene for this enzyme. Similarly, inhibitors of brain monoamino oxidase, by producing, in effect, a (partially) null phenotype of the gene for this enzyme, act as tranquilizers or antidepressants. Acetylsalicyclic acid (aspirin), by inhibiting a specific enzyme involved in the synthesis of one of the prostaglandins, produces a (partially) null phenotype of the gene for this enzyme, thereby inhibiting the synthesis of specific prostaglandins and, as result, reducing inflammation.

In a different example, "antisense" oligonucleotides, by binding, via Watson-Crick base pairing, to a region of the "sense" strand of a specific mRNA, interfere with its translation, for instance, by inhibiting the binding of initiation factors to the 5'-region of the mRNA. This inhibition, in effect, produces a (partially) null phenotype of a gene whose mRNA is targeted by the oligonucleotide.

The above "null phenotype" terminology, while not yet widely used, makes possible a unifying description of a variety of pharmacological (inhibitor-based) and genetic (gene manipulation-based) interventions whose common feature is inhibition of the functions of specific proteins or protein complexes.

An alternative approach to specific null phenotypes is based on constructing dominant negative mutations (reviewed by Herskowitz, I., Nature 329:219-222 (1987)). The latter, by definition, perturb the function of a protein of interest even in the presence of its wild-type version, for instance, by introducing a mutuant form of a protein that forms a functionally inactive complex with the protein of interest.

Figures 4A, 4B:
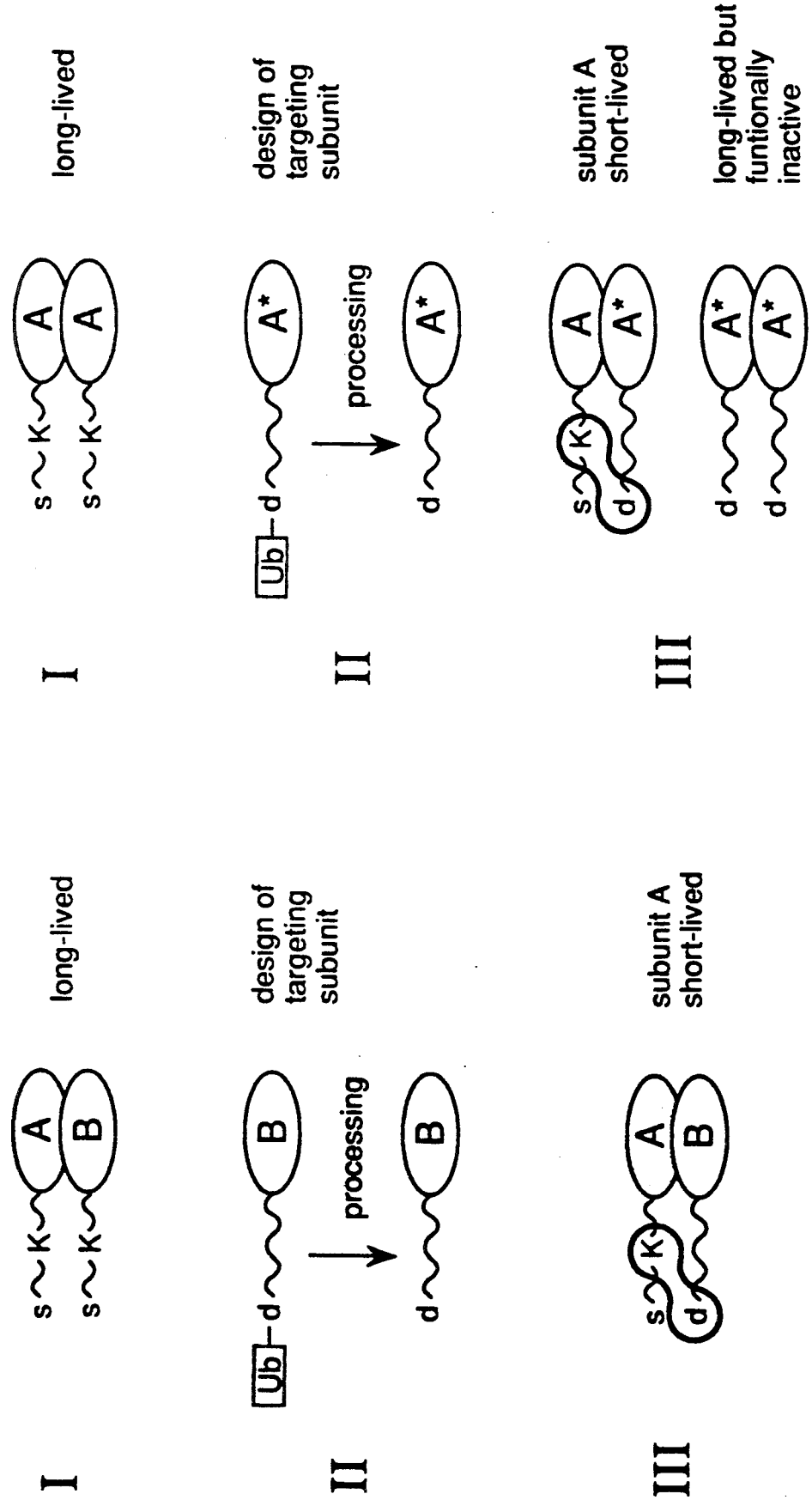
FIGS. 4A and B are diagrams illustrating the use of trans recognition to metabolically destabilize a protein of interest.

As shown below, the existence of trans recognition in the N-end rule pathway and the subunit specificity of selective protein degradation allow construction of a new class of dominant negative mutations that is the subject of the present patent application. The distinguishing feature of this new class is selective metabolic destabilization of an otherwise long-lived protein of interest by targeting it for degradation in trans. Decreasing metabolic stability of a protein lowers its concentration in the cell, thereby providing an alternative route to the null phenotype. One version of the trans-degradation approach, illustrated in FIGS. 4A and B, requires a gene for a protein (or a portion thereof) that specifically interacts with the protein or peptide of interest. (Most natural proteins exist as either dimers or higher oligomers; even those proteins that occur as monomers in vitro, in most cases interact with other proteins during their functioning in vivo.) The gene for a targeting protein or peptide that specifically interacts with the protein or peptide of interest is modified, for example, by using the previously developed ubiquitin fusion technique (FIGS. 3A to C; Bachmair et al., *Science* 234:179-186 (1966); Bachmair and Varshavsky, *Cell* 56:1013-1032 (1989)), to encode a variant of the targeting protein or peptide that, upon its in vivo expression, bears a destabilizing amino-terminal residue but lacks an efficient second determinant (multiubiquitination site) of the N-end rule-based degradation signal. In vivo production of the targeting protein or peptide would result in complex formation with the protein or peptide of interest, which could then be targeted for degradation in trans (FIGS. 4A and B). A remarkable feature of this new approach, stemming from the subunit specificity of protein degradation, is that the targeting protein, lacking the second determinant of the degradation signal, would not be destroyed. It therefore acts catalytically rather than stoichiometrically in trans-targeting the protein of interest for selective degradation.

In FIGS. 4A and B, ovals "A" and "B" represent polypeptide subunits. The first determinant of the N-end rule-based degradation signal (an amino-terminal amino acid residue) is designated "s" for stabilizing, or "d" for destabilizing. The second determinant of the N-end rule-based degradation signal (a specific lysine residue) is designated "K". Ubiquitin is designated as "Ub" in FIGS. 4A and B. As illustrated in FIGS. 4A and B, the trans-degradation technique is applicable to either homomeric (FIG. 4B) or heteromeric (FIG. 4A) targets. Specifically, to destroy a subunit A in a long-lived AB heterodimer, a modified subunit B bearing a destabilizing amino-terminal residue and lacking an efficient second determinant of the degradation signal is introduced into a cell, for instance, by expressing it from a vector encoding the modified subunit B (FIG. 4A). Targeting for degradation a long-lived homodimer AA is similar to the above method except that the targeting subunit is additionally modified to encode a variant (A*) of the subunit A that is functionally inactive at least as a homodimer (d-A*/D-A*). Introduction of a thus modified subunit A* into a cell leads either to a heterodimer in which the modified subunit d-A* trans-targets the subunit A for degradation or to a long-lived but functionally inactive d-A*/d-A* homodimer (FIG. 4B).

Since protein-protein interactions often involve relatively short contiguous amino acid sequences that retain their binding specificity as peptides (O'Shea et al., *Science* 245:646-648 (1989)), the latter, or their cell-penetrating chemical analogs, should also be of use in the trans-degradation approach. Furthermore, while the experimental demonstration of the possibility of trans recognition is confined, at present, to the N-end rule-based degradation signal, trans recognition is likely also to be characteristic of other degradation signals in proteins. Features of a degradation signal that should make it a candidate for the cis/trans recognition are the presence of more than one distinct determinant and the lack of a strict "linear" distance constraint on the determinants' arrangement. The experimental approaches that have been used to show that the N-end rule-based degradation signal is a multi-component one, and can function either in cis or in trans, can readily be adapted to dissect, in a similar manner, other degradation signals in short-lived proteins, and to establish whether the cis/-trans recognition, and hence, the methods of the present invention, are relevant to these signals as well. As shown below, subunit specificity in protein degradation, another independent element of the trans-degradation approach, is not confined to the N-end rule pathway, inasmuch as at least one of the degradation signals in a naturally short-lived yeast $\alpha 2$ repressor operates in a subunit-specific manner.

With the analysis of the N-end rule-based degradation signal and of the degradation signals present in $\alpha 2$ repressor having established a way to approach the above questions, those skilled in the art can determine directly, for any degradation signal encountered, whether the trans-degradation approach of the present invention is a relevant and applicable one.

In another aspect, the present invention relates not only to the targeting proteins of peptides that interact with mature forms of a protein of interest, but also to the targeting proteins or peptides that interact with incompletely folded forms of a protein or peptide of interest in vivo. Every in vivo-synthesized protein must undergo conformational maturation, a process that converts a relatively disordered polypeptide chain of a protein as it emerges from the ribosome into a well-defined folded structure that is characteristic of a mature protein. Although some aspects of this complex process are understood, the actual folding pathways are known for very few proteins in vitro, and for virtually no proteins in vivo, where folding pathways may not be identical or even similar to those in vitro. The reasons for this latter complication include the presence of many other proteins in a cell, some of which may interact with the nascent protein of interest, and also the fact that, while in vitro folding assays usually start with an unfolded full-length protein, the folding in vivo starts while the protein's carboxyl-terminal region is still emerging from the ribosome.

A recent study by Hall and Frieden (*Proc. Natl. Acad. Sci. USA* 86:3060-3064 (1989)), using a model protein dihydrofolate reductase (DHFR), has shown that some fragments of DHFR can inhibit the in vitro refolding of the same full-length DHFR from its initially unfolded (denatured) state. Furthermore, these authors showed that some DHFR fragments inhibited the folding of the full-length DHFR much more effectively than others, i.e., that the inhibition effect is extremely sensitive to fragment sequence and composition. These results have led Hall and Frieden to propose the use of protein fragments as probes to study the mechanisms of protein folding in vitro.

The discovery of trans targeting and subunit-specific degradation of mature (folded) proteins makes possible a new application of the in vitro findings of Hall and Frieden. Specifically, folding-interfering targeting peptides whose amino acid sequence is identical or substantially homologous to a portion of the amino acid sequence of a protein or peptide of interest, can be used to target the protein of interest, in trans, for either degradation or functional impairment in vivo. In the in vitro approach of Hall and Frieden, the few fragments of DHFR that have actually been used were chosen for reasons of their relative ease of preparation rather than for their expected effect on the DHFR folding. In contrast, our method, in addition to being in vivo-based and protein degradation-oriented, provides for a systematic genetic approach to ascertain directly, for any protein of interest, which of its fragments are the ones that most effectively interfere with the folding, function and/or metabolic stability of the full-length protein.

Figure 5:
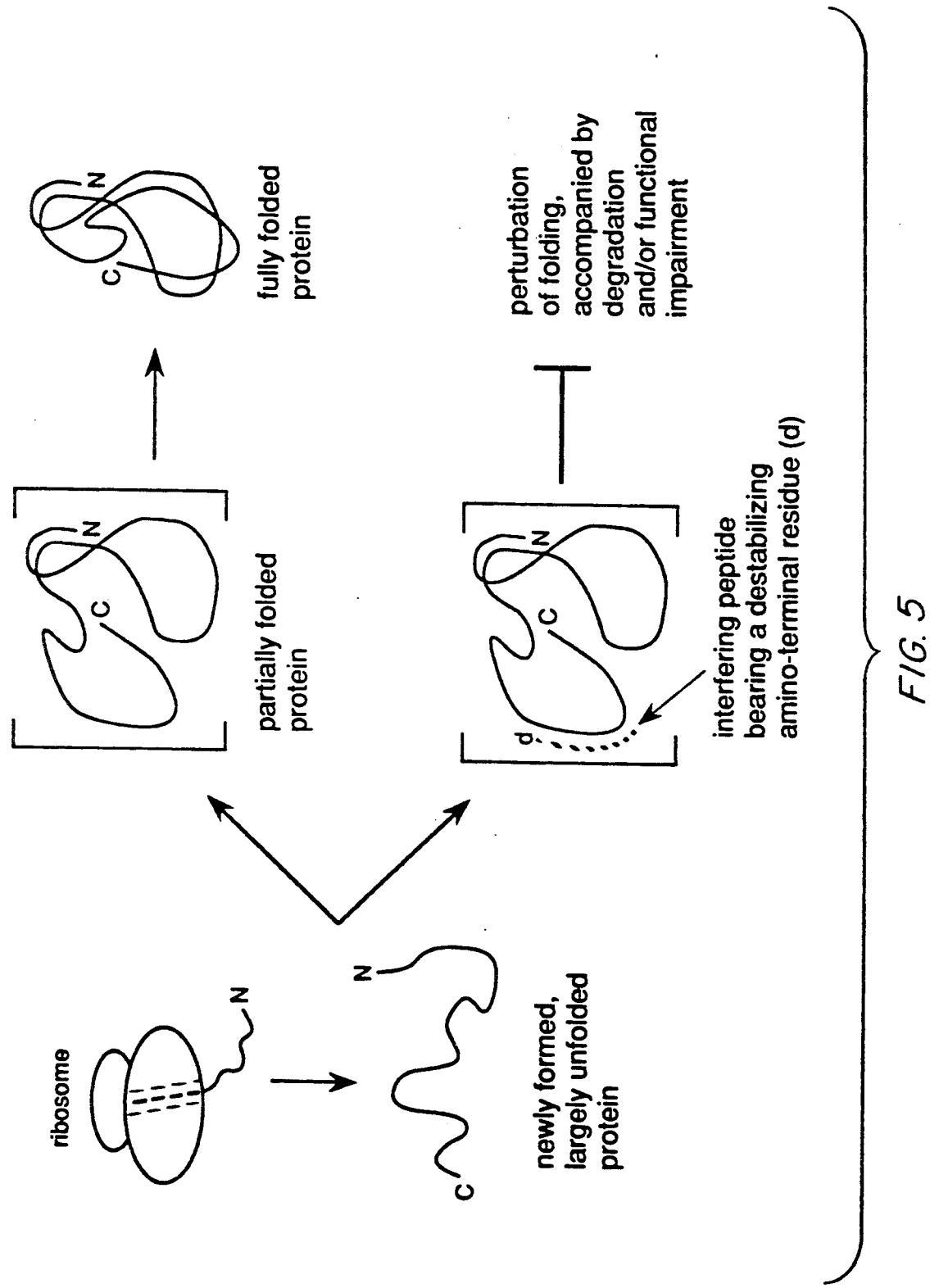
FIG. 5 is a diagram illustrating the use of peptides having an amino acid sequence identical or substantially homologous to a portion of the amino acid sequence of a protein of interest to metabolically destabilize a protein of interest in vivo.

FIG. 5 illustrates the use of a folding-interfering peptide to target a protein of interest for degradation. The interference can occur either during the folding of the full-length protein, as shown in FIG. 5, or even during folding of the amino terminus-proximal region of the protein as it emerges from the ribosome.

If a folding-interfering targeting peptide interrupts the folding of a protein (from which the peptide had been derived) either irreversibly or at least for a relatively long period of time before a dissociation event and the resumption of folding, the resulting functional impairment of the protein of interest will be obtained in vivo even in the absence of the accompanying metabolic destabilization (destruction) of the targeted peptide-protein complex. However, since such a trapped complex would be likely to resemble a "misfolded" protein to the intracellular "surveillance" proteolytic pathways, it is likely that the effective decrease in the concentration of an active protein species in a cell would be caused by a combination of functional impairment and actual degradation of a targeted complex by the above proteolytic pathways. Whether a trapped peptide-protein complex (FIG. 5) would be degraded or whether it would remain long-lived but functionally inactive will depend on the amino acid sequences of the protein of interest and the folding-interfering targeting peptide (whose sequence is either identical or homologous to a subset of the sequence of the protein of interest).

To increase the probability that a trapped peptide-protein complex will be short-lived in vivo, a folding-interfering targeting peptide can be designed to be produced as a ubiquitin-peptide fusion whose efficient in vivo deubiquitination (FIGS. 3A to C) would generate a predetermined destabilizing residue at the peptide's amino terminus (FIG. 5). When such a peptide traps a folding protein of interest, its destabilizing residue makes possible trans targeting of the (partially folded) trapped protein of interest for degradation via the N-end rule pathway, as discussed above (FIGS. 2A to C). Moreover, a protein species trapped by the targeting peptide is by definition partially folded (FIG. 5). The inevitable conformational instability of this species (relative to the folded species of the same protein) is expected to provide additional conformationally mobile lysine residues that could serve as second determinants (ubiquitination sites) of the N-end rule-based degradation signal. Thus, the N-end rule-mediated trans targeting of a trapped peptide-protein complex is expected to be unusually efficient because of the lack of conformational stabilization of lysine residues (potential second determinants of the degradation signal) within an incompletely folded protein of interest. Furthermore, once the best (i.e., most efficient) of the folding-interfering targeting peptides are identified for a given protein of interest, (see FIG. 6 and discussion below), it is a routine matter to substitute the peptides' lysine residues (if any are present) for homologous nonubiquitinatable (arginine) residues, so that no cis-recognition of the peptide itself is possible by the N-end rule pathway. Expressing targeting peptides as ubiquitin fusions will temporarily stabilize these peptides against intracellular degradation, as has previously been found for several otherwise short-lived peptides fused to ubiquitin moieties (Finely et al., *Nature* 338:394–401 (1989)). Thus, while a multi-ubiquitin chain is a signal for protein degradation (see e.g., FIGS. 1 and 2A to C, an amino-terminal monoubiquitin moiety can increase (under certain conditions identified by Finley et al.) the in vivo half-life of a protein or peptide moiety located "downstream" of the ubiquitin moiety.

Since the number of possible fragments of even a moderately sized protein of interest is quite large, the method of this invention, to be generally applicable, should provide for a systematic, assumption-free way to distinguish between efficiently and inefficiently acting folding-interfering targeting peptides, and to identify positively the former for any given protein of interest. A genetically based, generally applicable method that provides for such an identification is presented in FIG. 6.

Figure 6:
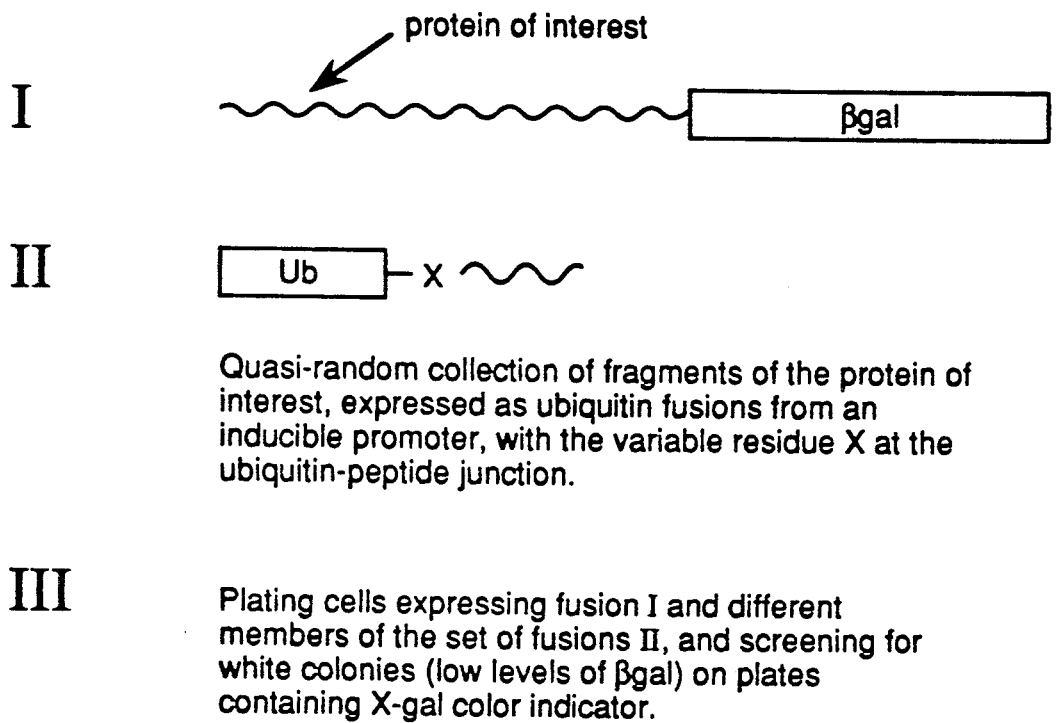
FIG. 6 is a diagram illustrating the use of a genetic screen to identify polypeptides having an amino acid sequence identical or substantially homologous to a portion of the amino acid sequence of a protein of interest that metabolically destabilize the protein of interest in vivo.

Initially, a fusion of a protein of interest with a marker protein, such as β-galactosidase (βgal), is provided in a host cell. A construct encoding such a fusion can be made, for example, by fusing a gene encoding a protein of interest to a gene encoding a marker protein such as βgal to yield a fusion protein containing the moiety of the protein of interest in front of the βgal moiety (FIG. 6-I). Thereafter, a DNA library encoding ubiquitin fusions to various fragments of the protein of interest is constructed (FIG. 6-II). One way to construct such a library is as follows:

(i) A set of genes encoding carboxyl-terminally truncated derivatives of the protein of interest is obtained by making stepwise deletions from the 3'-end of a gene encoding the protein of interest. Such "nested" deletion techniques are well known to those skilled in the art (see e.g., Sambrook et al., *Molecular Cloning*, Cold Spring Harbor Laboratory, N.Y. 1989).

(ii) In a similar manner, a set of stepwise amino-terminal deletions of the protein of interest is constructed. The total mumber of different deletion derivatives that retain one mature end of the protein of interest (either the carboxyl-terminal or the amino-terminal end) is made as close as possible to twice the number of amino acid residues in the protein of interest (there are as many possible carboxy-terminally truncated derivatives of a protein as there are amino acid residues in the protein; the same is true of amino-terminally truncated derivatives).

(iii) In a separate cloning step, genes encoding the amino-terminally truncated derivatives of the protein of interest are subjected to stepwise carboxyl-terminal deletions, to yield as set of genes encoding internal fragments of the protein of interest.

(iv) All three classes of the genes encoding deletion derivatives thus produced (internal, carboxyl-terminal, and amino-terminal) are fused to a gene encoding the upstream ubiquitin moiety, either with an additional (predetermined) residue X at the ubiquitin-peptide junction, or without such a residue.

(v) Either yeast (e.g., *S. cerevisiae*) or bacterial (e.g., *E. coli*) cells lacking β-galactosidase are transformed with an expression vector encoding the target protein of interest fused to βgal (FIG. 6-I), and thereafter transformed with the above-described library of genes encoding different fragments of the protein of interest and carried in the background of an expression vector with an inducible promoter (for instance, GAL promoter in the yeast *S. cerevisiae* or Ptrc promoter in *E. coli*).

(vi) Transformants from step (v) are grown on a solid medium containing X-Gal, a color indicator for βgal activity (Sambrook et al., *Molecular Cloning*, Cold Spring Harbor Laboratory, N.Y., 1989), and screened for light blue or white colonies (i.e., those producing little or no βgal) under conditions where an inducible promoter of step (v) is active.

(vii) If any such colonies are found, the corresponding transformants are retested under conditions where an inducible promoter of step (v) is inactive (little or no expression of folding-interfering targeting peptide). If the transformants thus tested are blue in the absence of peptide expression but white or light blue in the presence of peptide expression, the corresponding cell clones are subjected to a more detailed analysis. In particular, plasmids encoding specific ubiquitin-peptide fusions are isolated from the above transformants, and the sequence of the corresponding peptide(s) is established by determining nucleotide sequence(s) of the corresponding gene(s). These ubiquitin-peptide fusions are then independently transformed into cells that express the original protein-βgal target (FIG. 6-I), to confirm that the peptide indeed strongly decreases βgal activity in the recipient cells. More detailed experiments could also be carried out to characterize the folding-interfering peptide(s), for instance, a direct determination of the metabolic fate of a test βgal fusion (FIG. 6-I) in the presence or absence of the folding-interfering targeting peptide's expression. This determination is carried out by pulse-chase analysis (Bachmair et al., *Science* 234:179-186 (1986)), a method well known to those skilled in the art.

The rationale for experimental steps described above and in FIG. 6 is as follows. If an efficient folding-interfering peptide prevents or otherwise interferes with the conformational maturation of a protein of interest in vivo, the resulting (trapped) peptide-protein complex and downstream βgal moiety would be likely to be targeted for degradation for the reasons indicated above. As a consequence, the steady-state level of βgal would decrease either moderately or strongly, depending on the efficiency of a folding-interfering targeting peptide, and the resulting change in βgal activity could be detected by the X-Gal-based screen described above (FIG. 6). The method illustrated in FIG. 6 makes possible direct detection and identification of those fragments of a protein of interest that target the protein of interest, in its fusion to βgal, for degradation in vivo. This method is applicable to any protein for which a gene is available, is essentially assumption-free in its execution, and is technically straightforward, in that all relevant procedures are well known to those skilled in the art.

The method illustrated in FIG. 6 cannot detect folding-interfering targeting peptides that, while perturbing the folding of the protein, do not target it for degradation. Although such fragments are unnecessary for the purpose of this invention (since folding-interfering, degradation-targeting fragments of the protein of interest are expected to be not infrequent), these fragments could also be identified by the approach illustrated in FIG. 6 if a functional activity of the protein of interest could be adapted to either a selection-type or a screen-type test, thereby bypassing the need for a marker protein moiety. In this case, a protein itself (rather than its fusion to βgal or another marker protein) would serve as a marker, with the rest of the FIG. 6 method intact.

Once the most efficient folding-interfering targeting peptides are identified through the method of FIG. 6 or its equivalents, these targeting peptides could be modified to make them more resistant to degradation in vivo. Moreover, "second-generation" targeting peptides could also be designed that, while equivalent in their folding-interfering capacity to the originally identified peptides, would be capable of penetrating cells directly, thereby obviating the necessity of expressing these peptides via DNA constructs from within cells.

The invention is illustrated further by the following examples.

EXAMPLES

Example 1

The N-end rule-based degradation signal in a short-lived protein comprises a destabilizing amino-terminal residue and a specific internal lysine residue (Bachmair, A. et al., *Science* 234:179-186 (1986); Varshavsky, A. et al., in *Ubiquitin* (ed. Rechsteiner, M.) 287-324 (Plenum, New York, 1988); Bachmair, A. and A. Varshavsky, *Cell* 56:1019-1032 (1989); Cahu, V. et al., *Science* 243:1576-1583 (1989); and Gonda, D. K. et al., *J. Biol. Chem.* 264:16700-16712 (1989); see also FIG. 7). In this example, it is shown that, in a multisubunit protein, these two determinants can be located on different subunits and still target the protein for destruction. Moreover, in this case (trans recognition) only the subunit that bears the second (lysine) determinant is actually degraded. Thus, an oligomeric protein can contain both short-lived and long-lived subunits.

Trans Recognition in the N-End Rule Pathway

In a monomeric substrate of the N-end rule pathway, both determinants of the degradation signal are located, by definition, within the same polypeptide chain, and are therefore said to be recognized in cis (FIGS. 1 and 2A). However, in the case of a multisubunit protein, such as an X-βgal tetramer, the targeting of an individual X-βgal subunit might be influenced by the presence of other subunits in the tetramer. In particular, one can consider the possibility of trans recognition, in which the first and second determinants of the degradation signal reside within different subunits of X-βgal (FIG. 2B, C). One can also ask whether the targeting and degradation components of the N-end rule pathway distinguish between those subunits of an X-βgal heterotetramer that carry the degradation signal from those that do not, or whether an entire tetramer is targeted for destruction even if only some of its subunits carried degradation signals (FIG. 2C). (To simplify the discussion, the cis and trans concepts are illustrated in FIGS. 2A to C for a dimeric protein. The $D_2$ symmetry and related properties (Edwards, L. A. et al., *J. Biol. Chem.* 263:1848-1858 (1988); Kania, J. and D. T. Brown, *Proc. Natl. Acad. Sci. USA* 73:3529-3533 (1976)) of the βgal tetramer suggest that its amino-terminal regions rae spatially close within each pair of dimers forming the tetramer, but distant between the dimers.) To follow the fate of individual X-βgal subunits within an X-βgal tetramer, we prepared radioactively labeled Ub-X-βgal heterotetramers the bulk of which contained one labeled and three unlabeled subunits per tetramer (FIG. 9A), and used these proteins to address the questions stated above.

Figure 8A:
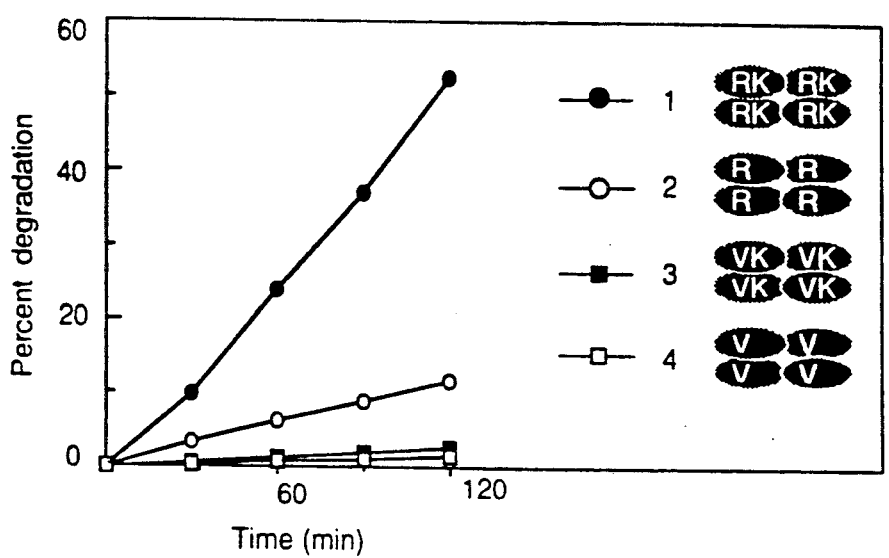
FIGS. 8A and B are diagrams illustrating ATP-dependent ubiquitination and degradation of X-$\beta$gal homotetramers in reticulocyte extract.
Figure 9B:
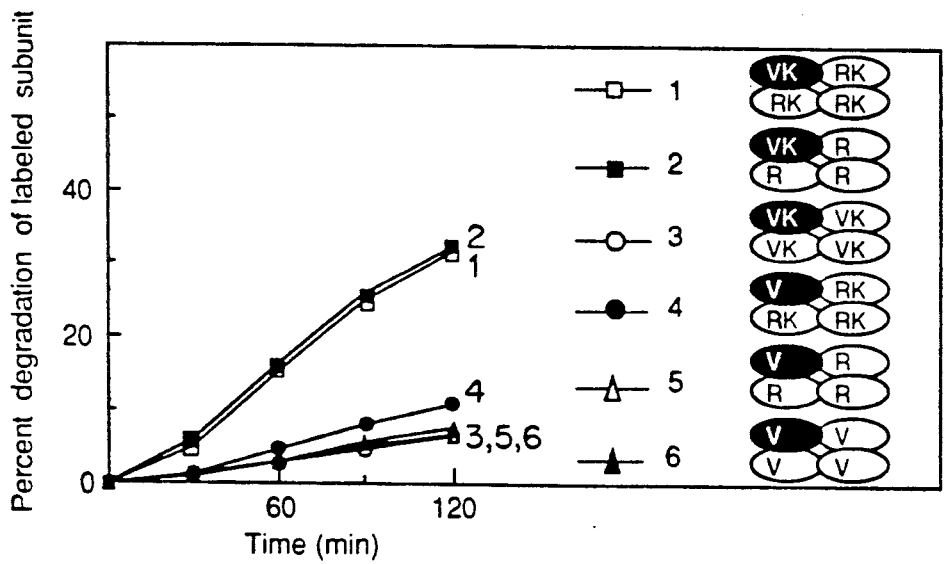
FIGS. 9A to D are diagrams illustrating ATP-dependent ubiquitination and degradation of X-$\beta$gal heterotetramers in reticulocyte extract.

FIGS. 8A and B and 9A to D illustrate the ATP-dependent ubiquitination and degration of X-βgal homotetramers and heterotetramers, respectively. The results show the kinetics of degration in ATP supplemented reticulocyte extract of $^{35}$S-labeled X-βgal proteins bearing either a stabilizing (Val) or destabilizing (Arg) amino-terminal residue, and either containing or lacking the second determinant of the degradation signal. Before describing the results of the mixed oligomer approach, it is noted that the reconstituted V~K~βgal*/V~K~βgal tetramer (the $^{35}$S-labeled subunit is designated with an asterisk) was degraded in reticulocyte extract at a slightly higher rate than the initial V~K~βgal tetramer that had not been subjected to the dissociation/reassociation treatment ($t_{\frac{1}{2}}$ of ~20 h and ~50 h, respectively; FIG. 8A, curve 3; FIG. 9B, curve 3).

This degradation, while ATP-dependent, was not mediated by the N-end rule pathway, because the labeled subunit within the reconstituted V~ΔK~βgal*/V~ΔK~βgal tetramer (all of whose subunits lacked both determinants of the degradation signal) was degraded in reticulocyte extract at a similar rate (FIG. 9B, curves 3 and 6). This additional slow degradation was therefore the background of our assays with reconstituted X-βgal tetramers. All of the time courses in FIGS. 9A to D were quantitatively reproducible both within and between different experiments.

When the labeled V~K~βgal subunit was present within the V~K~βgal*/R~K~βgal heterotetramer, it was multiply ubiquitinated and degraded in reticulocyte extract with a $t_{\frac{1}{2}}$ of ~3.3 h (FIG. 9B, curve 1). In contrast, when the same V~K~βgal subunit resided in the V~K~βgal*/V~K~βgal tetramer, its $t_{\frac{1}{2}}$ was 20 h, and it showed very little ubiquitination (FIG. 9B, curve 3). In a control experiment, the labeled V~K~βgal homotetramer was mixed with an excess of the unlabeled R~K~μgal homotetramer, and incubated in reticulocyte extract without the dissociation/reassociation pretreatment. Under these conditions, V~K~βgal was long-lived, with a $t_{\frac{1}{2}}$ of ~50 h, identical to the $t_{\frac{1}{2}}$ of V~K~βgal in the absence of R~K~βgal (FIG. 8A, curve 3).

Figure 7:
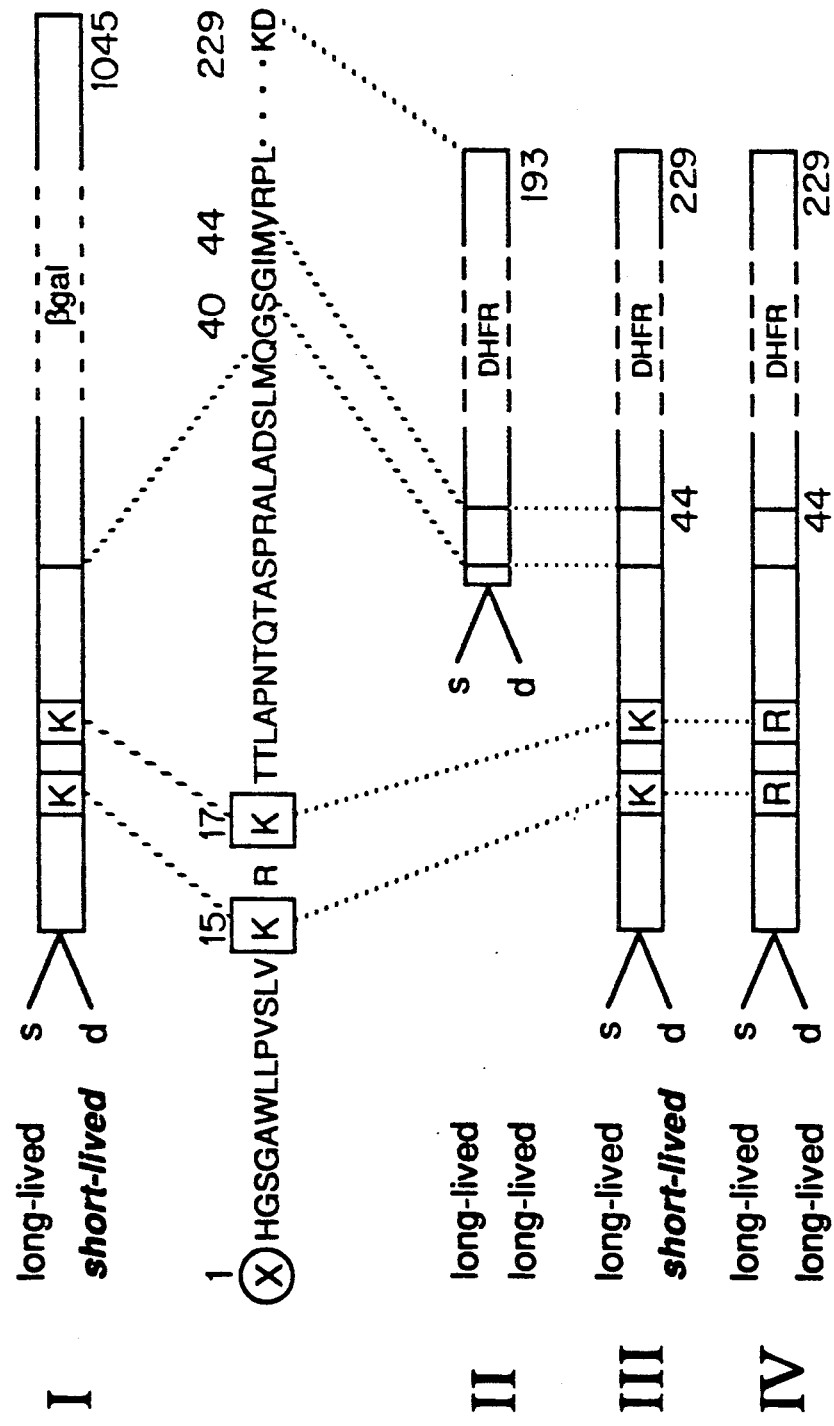
FIG. 7 is a diagram illustrating several genetic constructs and their use in dissecting the N-end rule-based degradation signal.

Taken together, these results indicated that a subunit bearing a stabilizing amino-terminal residue can be metabolically destabilized if it is physically associated with subunits containing the N-end rule-based degradation signal. These results also suggested the existence of trans recognition in the N-end rule pathway (FIG. 2B), i.e., that recognition of a destabilizing amino-terminal residue in an R~K~βgal subunit of the V~K~βgal*/R~K~βgal tetramer could promote multi-ubiquitination of the second-determinant lysine (Lys 15 or Lys 17; FIG. 7) in the V~K~βgal subunit of the same heterotetramer, resulting in the degradation of this otherwise long-lived subunit.

Remarkably, the metabolic instability of the V~K~βgal*/R~K~βgal heterotetramer did not depend on the degradation of the tetramer's intrinsically short-lived R~K~βgal subunits: the V~K~βgal subunit had a $t_{\frac{1}{2}}$ of ~3.3 h in reticulocyte extract within either V~K~βgal*/R~K~βgal or V~K~βgal*/R~ΔK~βgal (FIG. 9B, curves 1 and 2). The R~ΔK~βgal subunits of the latter heterotetramer lacked the second-determinant Lys 15/17 (FIGS. 1 and 7) and were, therefore, much longer-lived in reticulocyte extract than the otherwise identical R~K~βgal subunits (FIG. 8A, curves 1 and 2). Taken together, these results (FIG. 9B, curves 1-3) directly demonstrated the existence of trans recognition of short-lived subunits within X-βgal tetramers.

Figure 10A:
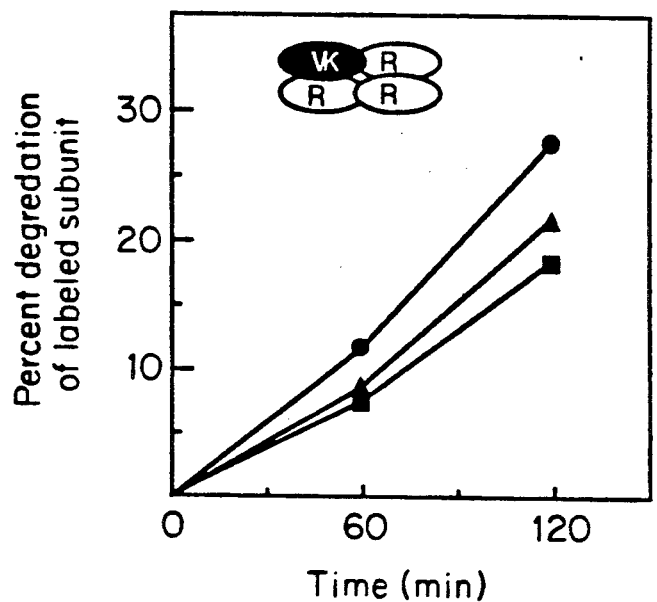
FIGS. 10A and B diagrams are illustrating trans recognition-dependent degradation of X-$\beta$gal subunits bearing a stabilizing amino-terminal residue.
Figure 10B:
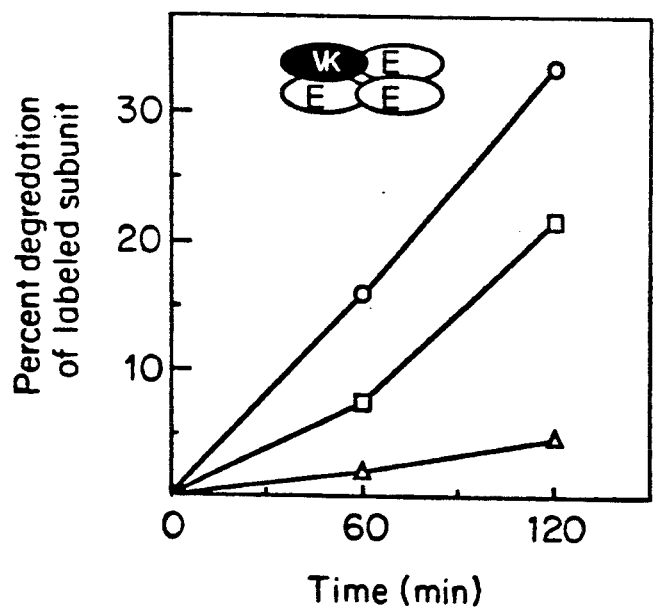

In an additional control experiment, we confirmed that the trans recognition-dependent degradation of X-βgal subunits bearing a stabilizing amino-terminal residue was, in fact, mediated by the N-end rule pathway. To do so, we exploited the previously established existence of secondary destabilizing residues in the N-end rule (Bachmair, A. et al., Science 234:179-186 (1986); Gonda D. K. et al., J. Biol. Chem. 264:16700-16712 (1989); Ferber, S. and A. Ciechanover, Nature 326:808-811 (1987)). Specifically, amino-terminal Glu (E) and Asp (as well as Cys in reticulocytes) are secondary destabilizing residues in that they function by virtue of their ability to be conjugated, via an Arg-tRNA-protein transferase, to a primary destabilizing residue, Arg (Gonda, D. K. et al., J. Biol. Chem. 264:16700-16712 (1989); Ferber, S and A. Ciechanover, Nature 326:808-811 (1987)). The Arg conjugation, and the resultant destabilizing property of a secondary destabilizing residue, can be selectively inhibited by a tRNA-depleting pretreatment of reticulocyte extract with RNAase (Gonda, D. K. et al., J. Biol. Chem. 264:16700-16712 (1989)). As shown in FIGS. 10A and B the labeled V~K~βgal subunit was short-lived within either the V~K~βgal*/R~ΔK~βgal or the V~K~βgal*/E~ΔK~βgal tetramer (the latter bearing E, a secondary destabilizing residue (Bachmair, A. et al., Science 234:179-186 (1986); Gonda, D. K. et al., J. Biol. Chem. 264:16700-16712 (1989); Ferber, S., and A. Ciechanover, Nature 326:808-811 (1987)) when they were incubated in reticulocyte extract. However, when the same assay was carried out in a tRNA-depleted reticulocyte extract, the V~K~βgal subunit in V~K~βgal*/E~ΔK~βgal became long-lived (FIG. 10B), in contrast to the same subunit in V~K~βgal*/R~ΔK~βgal, where it remained metabolically unstable (FIG. 10A). This result directly confirmed that the trans recognition-dependent degradation of the V~K~βgal subunit in a tetramer whose other X-βgal subunits bear destabilizing amino-terminal residues is mediated by the N-end rule pathway.

Figure 9C:
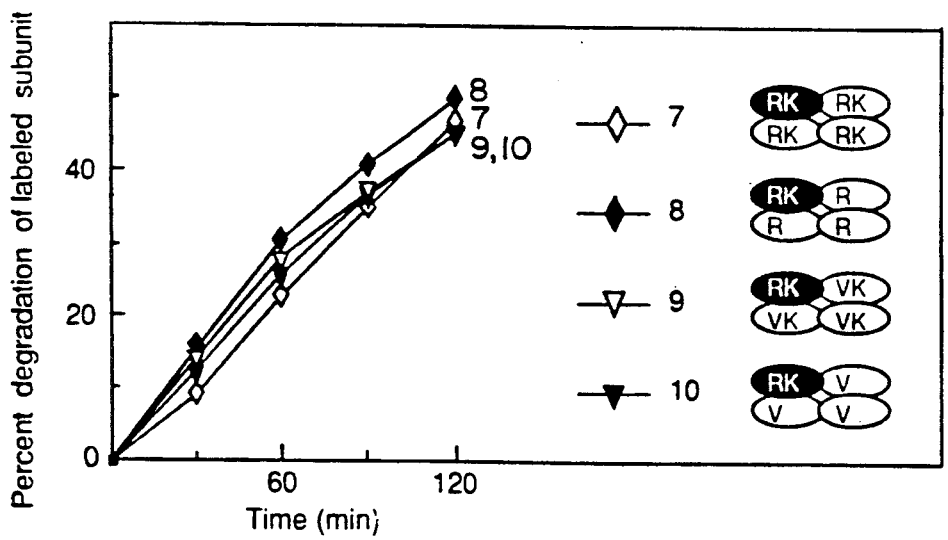
Figure 8B:
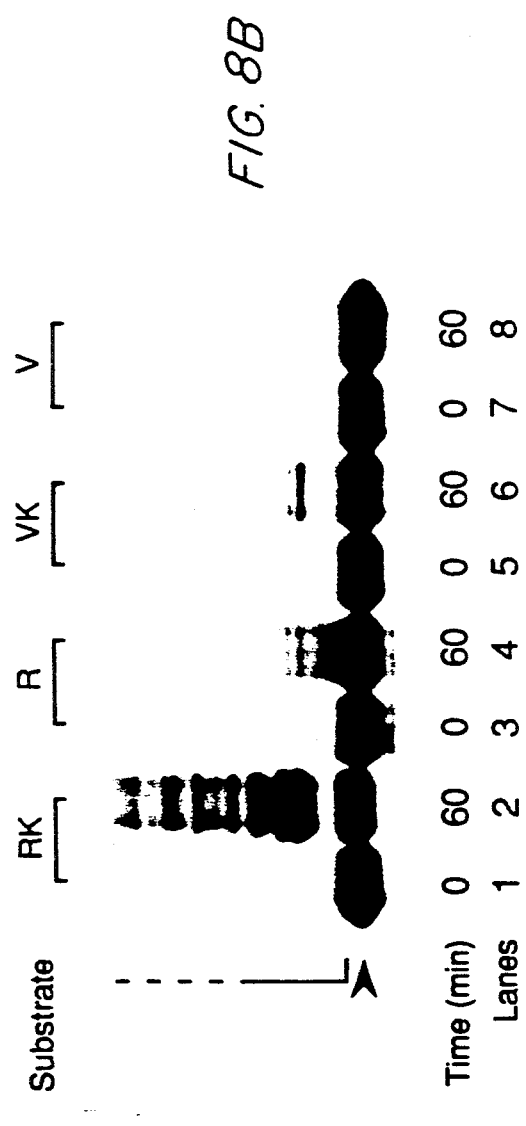
Figure 9D:
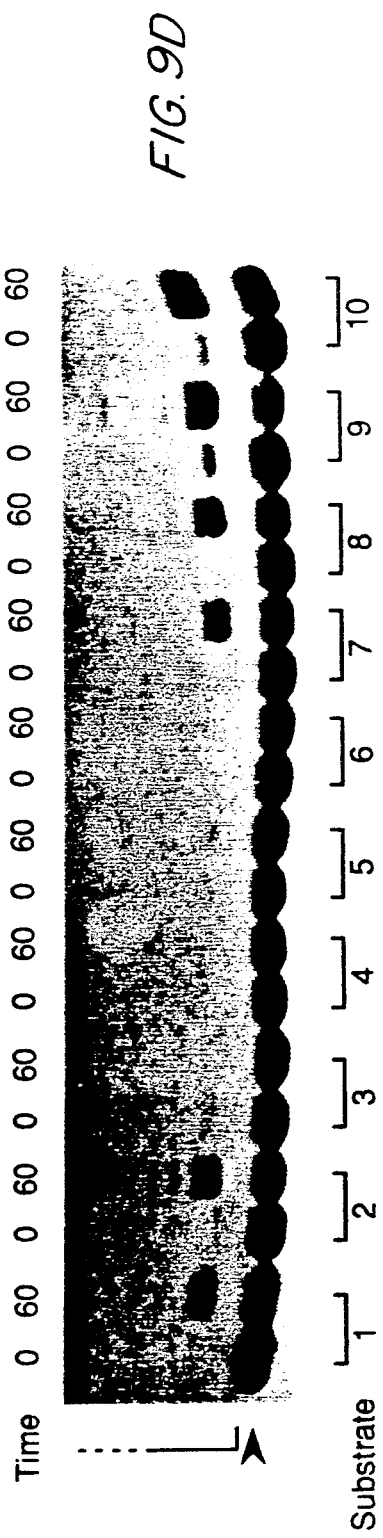
Figure 9A:
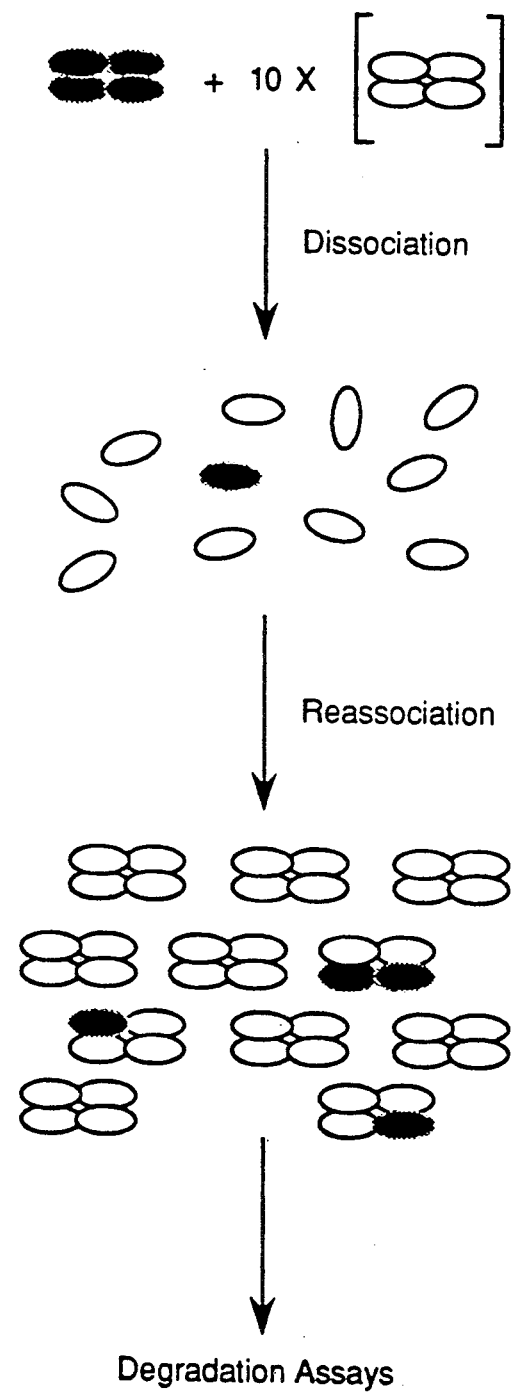

The Degradation of a Multisubunit Protein by the N-End Rule Pathway is Subunit-Specific While the labeled V~K~βgal subunit was short-lived within the V~K~βgal*/R~K~βgal tetramer, the otherwise identical V~ΔK~βgal subunit lacking the second-determinant Lys 15/17 (FIG. 7) was much more stable in the same tetramer background (FIG. 9B, curves 1 and 4). One implication of this result is that the trans-recognition-mediated degradation of a subunit bearing a stabilizing amino-terminal residue depends on the presence of the second determinant (multiubiquitination site) within the trans-targeted subunit. Remarkably, this result also indicated that an oligomeric protein can contain both short-lived and long-lived subunits. Indeed, while the V~ΔK~βgal subunit of V~ΔK~βgal*/R~K~βgal was long-lived in reticulocyte extract ($t_{\frac{1}{2}}$ of ~11.5 h; FIG. 9B, curve 4, the R~K~βgal subunits of this heterotetramer were much more unstable, with the R~K~βgal subunit of R~K~βgal*/V~ΔK~βgal having a $t_{\frac{1}{2}}$ of ~2.0 h (FIG. 9C, curve 10). Another implication of these results is that the degradation of short-lived subunits is not inhibited by the presence of long-lived subunits within the same oligomeric protein. Specifically, the $t_{\frac{1}{2}}$ of 2.0 h for the R~K~βgal subunit in reticulocyte extract was the same irrespective of whether this subunit was residing within a homotetramer (FIG. 9C, curve 7) or surrounded by the long-lived V~ΔK~βgal subunits (FIG. 9C, curve 10).

The differential degradation of individual subunits within X-βgal heterotetramers was not due to a rapid dissociation/reassociation of X-βgal subunits in reticulocyte extract that might allow short-lived subunits to be targeted and degraded while in a transient monomeric state. The βgal tetramer is known to be highly stable, requiring strongly denaturing solvents for its dissociation (Zipser, D., *J. Mol. Biol.* 7:113-121 (1963); Givol, D., et al., *Biochem. Biophys. Acta.* 113:120-125 (1966)). Furthermore, when labeled V~K~βgal homotetramers and an excess of unlabeled R~ΔK~βgal homotetramers were incubated together in reticulocyte extract, the V~K~βgal subunits were long-lived ($t_{\frac{1}{2}}$ of ~50 h), in contrast to the metabolic instability of the V~K~βgal subunit in the V~K~βgal\*/R~ΔK~βgal heterotetramer ($t_{\frac{1}{2}}$ of ~3.3 h; FIG. 9B, curve 2). It was concluded that the degradation of an oligomeric protein by the N-end rule pathway is subunit-specific.

Cis vs. Trans Recognition

X~K~βgal subunits bearing a stabilizing amino-terminal residue can be targeted for degradation only in trans (see above and FIG. 2B). On the other hand, the R~K~βgal subunit, which contains both determinants of the degradation signal, is targetable either in cis or in trans within R~K~βgal\*/R~K~βgal and R~K~βgal\*/R~ΔK~βgal, but only in cis within R~K~βgal\*/V~K~βgal and R~K~βgal\*/V~ΔK~βgal (FIGS. 2A to C and 9C). Nonetheless, the degradation time courses (as well as ubiquitination levels) of the R~K~βgal subunit in reticulocyte extract were indistinguishable for all of these tetramer backgrounds (FIG. 9C, curves 7-10).

These results indicated that the possibility of trans recognition does not increase the rate of degradation of an X-βgal subunit if the cis recognition mode is available as well. At the same time, for an X-βgal, trans recognition alone is comparable in efficiency to cis recognition alone, because the V~K~βgal subunit (targetable only in trans) was degraded within either V~K~βgal\*/R~K~βgal or V~K~βgal\*/R~ΔK~βgal at ~65% of the rate observed for the R~K~βgal subunits which could be targeted at least in cis ($t_{\frac{1}{2}}$ of ~3.3 h and ~2.0 h, respectively; FIG. 9B, curves 1 and 2; FIG. 9C, curves 7-10). The lack of influence of trans recognition in the presence of the cis recognition option is not due to inhibition of the trans mode of recognition by the cis mode, inasmuch as the V~K~βgal subunit was degraded at indistinguishable rates within either V~K~βgal\*/RR~K~βgal or V~K~βgal\*/R~ΔK~βgal (FIG. 9B, curves 1 and 2). A likely explanation of these results is that the cis recognition alone may be sufficient for the degradation of an X-βgal subunit to proceed at a rate limited by some other step in the N-end rule pathway.

On the Mechanism and Generality of Trans Recognition

The existence of trans targeting in the N-end rule pathway (FIGS. 2A to C, 9A to D and 10A and B) indicates that substrate recognition by this proteolytic system does not involve a linear "tracking" mechanism which might be used to ascertain, before the ubiquitination step, whether both determinants of the degradation signal are located within the same polypeptide chain. Trans targeting is therefore consistent with the previously proposed model (Bachmair, A. and A. Varshavsky, *Cell* 56:1019-1032 (1989)) in which an N-end-recognizing (E3) protein (either alone or complexed with a specific ubiquitin-conjugating (E2) enzyme) has a binding site for a substrate's destabilizing amino-terminal residue, and a lysine-binding site. Both of these sites must be occupied for the multiubiquitination to commence at the bound lysine of a proteolytic substrate. If the two binding sites of the recognition component are spatially fixed relative to one another, binding of the substrate would require either a specific spatial arrangement of the substrate's two determinants or a conformational mobility of these determinants relative to one another, so that their correct spatial arrangement is achieved transiently, but frequently enough for both of them to be bound by the recognition complex (Bachmair, A. and A. Varshavsky, *Cell* 56:1019-1032 (1989)).

Segmental mobility of the determinant-containing region (or regions) can account for both the cis and trans recognition in a short-lived X-βgal. Indeed, the non-βgal extension at the amino terminal of the X-βgal proteins (FIG. 7), being derived from an internal region of the lac repressor, is likely to be disordered (segmentally mobile) when present in an unnatural (amino-terminal) location within an unrelated protein such as βgal (Bachmair, A. and A. Varshavsky, *Cell* 56:1019-1032 (1989)). Because of segmental mobility of the extension, its Lys 15/17 residues (FIG. 7) could occur transiently in spatial proximity to a destabilizing amino-terminal residue of either their own or a different subunit within the same X-βgal tetramer, the latter allowing trans recognition.

Subunit Specificity in Protein Degradation

We have shown (FIGS. 9A to D and discussion above) that only those subunits of a metabolically unstable X-βgal tetramer that contain the second (but not necessarily the first) determinant of the degradation signal are actually degraded. In other words, the degradation is confined to those subunits that can be ubiquitinated. What might be the mechanism underlying this novel aspect of protein turnover? In one class of models, the selective (and apparently processive) (Chau, V. et al., *Science* 243:1576-1583 (1989); Hershko, A., *J. Biol. Chem.* 263:15237-15240 (b 1988)) degradation of a multiubiquitin chain-bearing subunit would be temporarily coupled to its dissociation from adjacent subunits within an oligomeric substrate. For this to occur, the ATP-dependent "downstream" protease (Hershko, A., *J. Biol. Chem.* 263:15237-15240 (1988)) would recognize the multiubiquitin chain (Chau, V. et al., *Science* 243:1576-1583 (1989)), use it to identify the subunit to destroy, and thereafter track along the subunit's polypeptide chain, presumably unfolding it before degradation. A priori, the dissociation and degradation need not be temporally coupled: a mechanochemical process analogous to the one above might be used to dissociate the multiubiquitin chain-containing subunit from an oligomeric substrate, with the degradation of the subunit following rather than accompanying its dissociation. (It has been shown above that spontaneous dissociation/reassociation of X-βgal subunits cannot account for the observed subunit specificity of X-βgal degradation by the N-end rule pathway.)

Subunit specificity is likely to emerge as a general feature of selective protein degradation because alteration of the functions of protein complexes via combinatorial variation of their subunit composition is a common theme in biological regulation (Abel, T. and T. Maniatis, *Nature* 341:24–25 (1989); Goutte, C. and A. D. Johnson, *Cell* 52:875–882 (1988)). For instance, many regulatory proteins are expressed in distinct but overlapping regions of a developing embryo, with cell determination depending at least in part on the exact combination of these proteins (many of which are short-lived) present in a given region at different stages of embryogenesis (Ingham, P. W., *Nature* 335:25–34 (1988); Scott, M. P. and S. B. Carroll, *Cell* 51:689–698 (1987)). Subunit-specific degradation may also underlie the periodic destruction of cyclin, a subunit of the multiprotein complex that regulates cell cycle progression in eukaryotes (Evans, T. et al., *Cell* 33:389–396 (1983); Murray, A. W. et al., *Nature* 339:280–286 (1989)). The two-determinant nature of a degradation signal, and the possibility of either cis or trans recognition may afford additional flexibility to subunit-specific degradation for instance, by making the accessibility of one of the determinants dependent upon specific phosphorylation events within a multisubunit substrate.

The generality of this new aspect of protein turnover is further supported by the recent finding that subunit-specific degradation is also characteristic of at least one of the two degradation signals present in the naturally short-lived transcriptional repressor MATα2 of the yeast *S. cerevisiae*. Neither of these signals operates via the N-end rule pathway (see Example 2).

Methods

The pKK233-2-based *E. coli* expression vectors pKKUb-Arg-βgal and pKKUb-Val-βgal encoding, respectively, Ub-R~K~βgal and Ub-V~K~βgal, have been described (gonda, D. K. et al., *J. Biol. Chem.* 264:16700–16712 (1989)). The constructs encoding Ub-R~ΔK~βgal and Ub-V~ΔK~βgal were made as follows. The small SalI/MstII fragment of pKKUb-Val-βgal was subcloned into M13 m18Δ (a derivative of M13m18 (Ausubel, F. M. et al., *Current Protocols in Molecular Biology*, Wiley-Interscience, New York, 1987) lacking the region between the AvaII and EcoRI sites), and oligonucleotide-directed mutagenesis (Ausubel, F. M. et al., *Current Protocols in Molecular Biology*, Wiley-Interscience, New York, 1987) was employed to generate a BglII site at the position encompassing codons 39 and 40 of the V~K~βgal reading frame. The small SalI/MStII fragment of the resulting construct was ligated to the vector-containing SalI/MstII fragment of pKKUb-Val-βgal. The large BamHI/BglII fragment of the construct obtained was ligated to the small BamHI fragment of the previously described Leu-DHFR construct V (Bachmair, A. and A. Varshavsky, *Cell* 56:1019–1032 (1989)), yielding pKKUb-Val~-ΔLys~βgal. Owing to the construction route taken, Leu-Ala at the positions 39–40 of the original V~K~βgal was replaced, in V~ΔK~βgal, by Gly-Ser. These changes were confined to the *E. coli* lacI-encoded 45-residue extension present at the amino termini of our X-βgal test proteins (Bachmair, A. and A. Varshavsky, *Cell* 56:1019–1032 (1989)). To construct pKKUb-Arg~ΔLys~βgal, the large SalI/BamHI fragment of pKKUb-Val~ΔLys~βgal was ligated to the small SalI/BamHI fragment of pKKUb-Arg-βgal. Ub-X-βgal proteins were expressed in *E. coli*, metabolically labeled with [$^{35}$S]methionine, and purified by affinity chromatography om aminoiphenylthiopyranogalactoside-(APTG)-agarase as described (Gonda, D. K. et al., *J. Biol. Chem.* 264:16700–16712 (1989)), except that 3 mCi of $^{35}$S-Translabel (ICN) were used for labeling, and that MgCl$_2$ was omitted from the final storage buffer. The specific radioactivity of Ub-X-βgal was 6–8×10$^5$ cpm/μg. Rabbit reticulocyte extract was prepared and assayed for the degradation of X-βgal proteins as previously described (Gonda, D. K. et al., *J. Biol. Chem.* 264:16700–16712 (1989)), including a 10-min preincubation in ATP-depleted extract (Gonda, D. K. et al., *J. Biol. Chem.* 264:16700–16712 (1989)) to deubiquitinate Ub-X-βgal. SDS-PAGE was carried out in 6.5% polyacrylamide, 0.18% bisacrylamide gels, with subsequent fluorography. The ATP- and ubiquitin-dependent degradation of X-βgal in reticulocyte extract obeyed first-order kinetics for at least the first 2 hours, making it possible to compare the degradation of different χ-βgal proteins by comparing their half-lives in the extract (Gonda, D. K. et al., *J. Biol. Chem.* 264:16700–16712 (1989)). The t$_\frac{1}{2}$ of R~K~βgal did not change when its initial concentration in the extract was reduced 20-fold.

Variants of Ub-X-βgal subunits were constructed, prepared (as homotetramers), and purified as described above. Total protein concentration was measured using the Bradford assay (BioRad). To prepare heterotetramers (Ullman, A. and J. Monod, *Biochem. Biophys. Res. Commun.* 35:35–42 (1969)) of UB-X-βgal, a mixture of 18 μg [$^{35}$S]Ub-X-βgal and 180 μg of unlabeled Ub-X-βgal (whose amino acid sequence was either identical to or different from that of the labeled Ub-X-βgal), at a total protein concentration of 1.5 to 3 mg/ml in storage buffer (50% (v/v) glycerol, 0.1 mM Na-EDTA, 1 mM dithiothreitol (DTT), 40 mM Tris-HCl (pH 7.5)), was diluted to a protein concentration of 80 μg/ml with buffer A (10 mM Na-EDTA, 5 mM DTT, 20 mM Na-HEPES (pH 7.2)) containing 2M NaCl and 8M (deionized) urea. After 1 hour at 0° C., the solution was dialyzed against changes of buffer A containing, successively, 8M urea, 4M urea and 10 mM NaCl, 2M urea and 10 mM NaCl, 1M urea and 10 mM NaCl, and finally, against two changes of buffer A pulse 10 mM NaCl. Dialysis was carried out with ten Ub-X-βgal samples at a time, at 4° C., in a Multiple Dialyzer (Spectrum), for ~14 h per change of buffer. Each of the dialyzed samples was brought to 1.6M in NaCl and 10 mM in MgCl$_2$, added to ~0.4 ml of APTG-agarose (Gonda, D. K. et al., *J. Biol. Chem.* 264:16700–16712 (1989)) and rocked overnight at 4° C. The suspension was then loaded into columns, which were processed for affinity purification of Ub-X-βgal as described (Gonda, D. K. et al., *J. Biol. Chem.* 264:16700–16712 (1989)). At a 1:10 ratio of labeled of unlabeled Ub-X-βgal subunits, random reassociation should result in 75% of the labeled subunits residing in tetramers containing one labeled subunit per tetramer, with most of the rest of the labeled subunits (23%) present at two subunits per tetramer. In a test of this prediction, a 1:10 mixture of two βgal-based homotetramers containing amino-terminal extensions of different sizes was subjected to the dissociation/reassociation protocol. Electrophoresis of the resulting tetramers in a non-denaturing gel produced the expected distribution of heterotetramer compositions. The enzymatic activity of the reconstituted Ub-X-βgal proteins (determined as described, Guarente, L., *Meth. Enzymol.* 101:181–182 (1983)) varied between different preparations from 50 to 75% of the activity of their initial (homotetramer) counterparts. Degradation assays in reticulocyte extract and SDS-PAGE were carried out as described above. Less than 0.4% of either the initial or reconstituted X-βgal tetramers were degraded in 2 h in ATP-depleted reticulocyte extract.

The pKKUb-Glu-ΔLys~βgal expression vector encoding Ub-E~ΔK~βgal was constructed as described for pKKUb-Arg~ΔLys~βgal above. Ub-X-βgal heterotetramers were prepared from the corresponding homotetramers as described above. The RNAase treatment (Gonda, D. K. et al., *J. Biol. Chem.* 264:16700-16712 (1989)) was carried out by incubating reticulocyte extract for 45 min at 37° C. with 3 units/ml of RNAase A-agarose (Sigma), centrifuging to remove the immobilized RNAase, and adding RNasin (RNAase inhibitor (Promega Biotech)) to 1500 units/ml. Reactions supplemented with tRNA included 50 μg/ml of purified total tRNA from bovine liver (Boehringer).

Example 2

Metabolic instability is characteristic of regulatory proteins whose in vivo concentrations must vary as function of time. The cell type-specific α2 repressor of the yeast *S. cerevisiae* is shown in this Example to have a half-life of only ~5 minutes. Each of the two structural domains of α2 carries a sequence that can independently target a normally long-lived protein for rapid destruction. Moreover, these two degradation signals are shown here to operate via distinct mechanisms. Mutants deficient in the degradation of α2 have been isolated and found to have a number of additional defects, indicating that the pathways responsible for α2 turnover include components with multiple functions. These insights have also allowed the demonstration that a short-lived subunit of an oligomeric protein can be degraded in vivo without destabilizing other, long-lived subunits of the same protein. In other words, it is shown below that at least one of the two degradation signals in α2 (both of which are distinct from the N-end rule-based signal) operates in a subunit-specific manner, thereby indicating that subunit-specific degradation is not confined to the N-end rule pathway.

Fusion of α2 to β-galactosidase Produces a Short-lived Protein

Figures 11A, 11D:
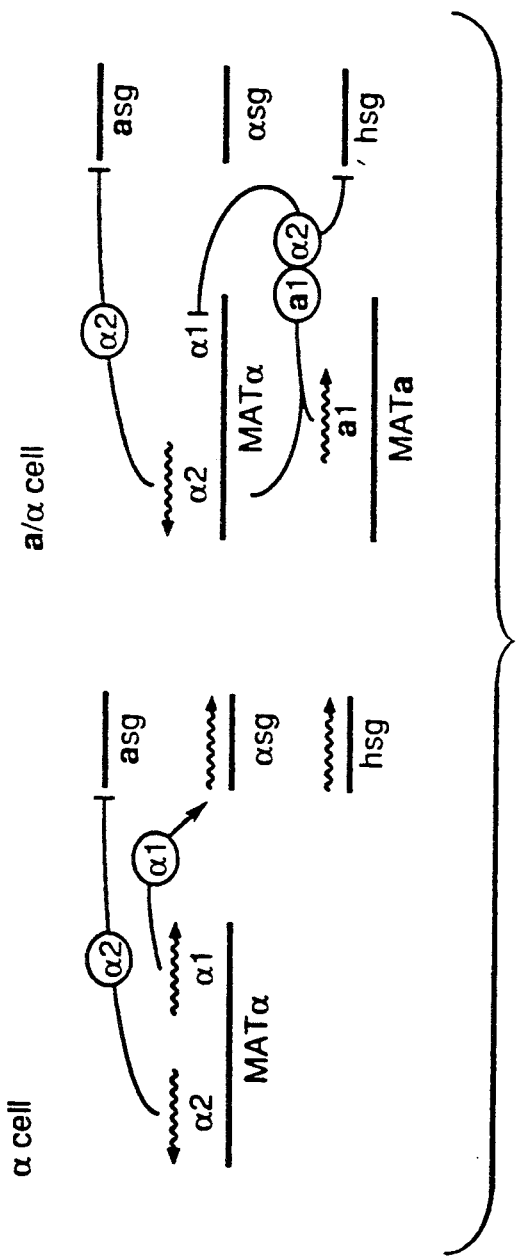
FIGS. 11A to D are diagrams illustrating the metabolic instability of an $\alpha$2-$\beta$gal fusion protein.
Figures 11B, 11C:
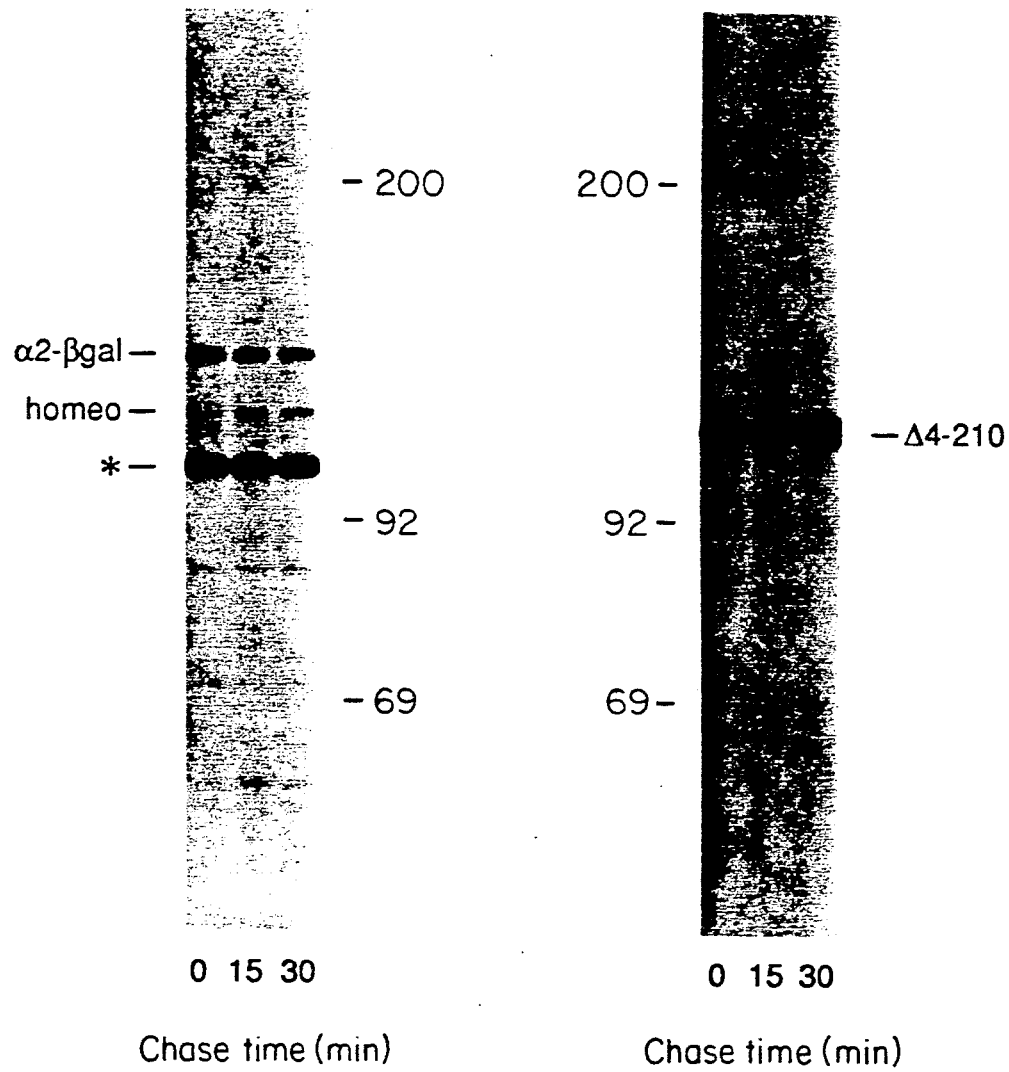

To study the in vivo degradation of α2, *E. coli* β-galactosidase (βgal) was used as an immunological tag, allowing immunoprecipitation of α2-βgal fusion proteins with a monoclonal antibody to βgal. Cells carrying a high copy plasmid encoding α2-βgal were labeled with [$^{35}$S] methionine for 7 minutes at 30° C., followed by a chase in the presence of translation inhibitors, extraction, precipitation with antibody to βgal, and SDS-PAGE. βgal that carried only the first 3 residues of α2 at its amino terminus was metabolically stable, with no detectable degradation during the chase period (FIG. 11C). In contrast, attachment of the full-length 210-residue α2 sequence to βgal yielded a short-lived protein (FIG. 11B).

The in vivo degradation of α2-βgal did not follow first-order kinetics but instead, slowed with time. A similar phenomenon has been observed with βgal derivatives designed to be degraded via the N-end rule pathway (Bachmair, A. et al., *Science* 234:179-186 (1986)). Since a single half-life cannot be assigned to a protein degraded with non-first order kinetics, "initial half-lives" were calculated (denoted below with quotation marks) by assuming first-order kinetics between the pulse (zero time) and the earliest chase time points (10 or 15 minutes). For example, the "$t_{\frac{1}{2}}$" of α2-βgal was ~15 minutes at 30° C.

A portion of the short-lived α2-βgal was converted to a smaller protein (homeo in FIG. 11B) that accumulated during the chase and was therefore likely to be the product of an in vivo cleavage. Amino acid sequencing of the purified cleavage product placed the major cleavage site within the DNA-binding homeodomain at α2 (Laughon, A. and M. P. Scott, *Nature* 310:25-31 (1984); Shepherd, J. C. W. et al., *Nature* 310:70-71 (1984); Porter, S. D. and M. Smith *Nature* 320:766-768 (1986); Hall, M. N. and A. D. Johnson, *Science* 237:1007-1012 (1987)), between residues 165 and 166 (FIG. 11D) in the positioning helix of the helix-turn-helix motif. The steady state concentration of the cleavage product was a much as 6-fold higher than that of the intact α2-βgal, at least in part because of its longer half-life (~2 hours). Since this cleavage is expected to inactivate the repressor, it may provide a mechanism for clearing α2 from its DNA binding sites during a switching from an α to an a cell; this possibility remains to be tested.

The Intact α2 Repressor is Extremely Short-lived

To examine the in vivo degradation of the unmodified α2 repressor, a polyclonal antibody to α2 was generated. This affinity-purified antibody specifically immuno-precipitated the 24-kD α2 protein from extracts of yeast α cells (FIG. 12A). By immunofluorescent staining using this antibody, it was also determined that α2 is a predominantly nuclear protein.

Figure 12C:
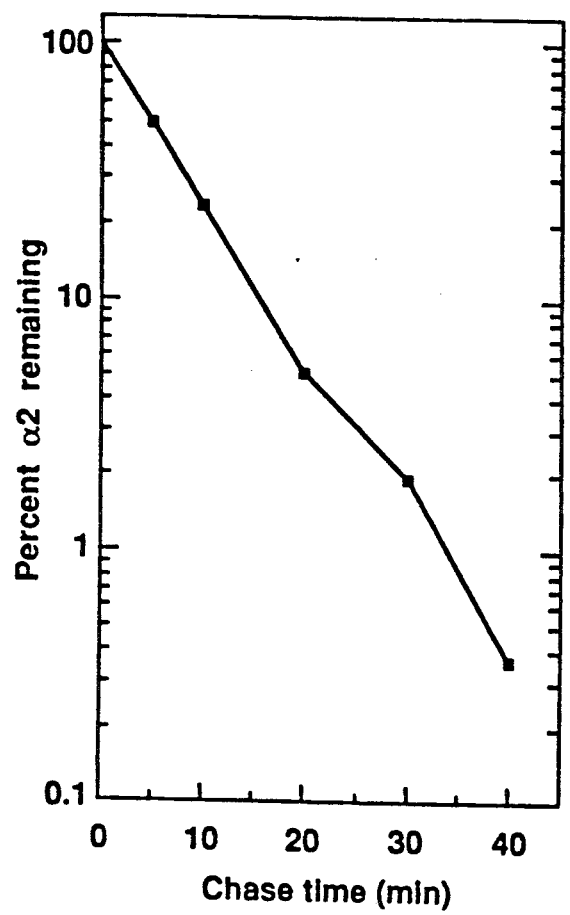

The α2 repressor was found by pulse-chase analysis to be extremely short-lived in vivo (FIGS. 12B, 12C). Its half-life of ~5 minutes at 30° C. was ~3-fold shorter than the "$t_{\frac{1}{2}}$" of the α2-βgal protein (FIG. 12B). Moreover, unlike α2-βgal, the intact α2 repressor was degraded with apparent first-order kinetics, indicating that most of the α2 molecules in the cell were equally susceptible to degradation. No discrete α2 degradation intermediates accumulated to detectable levels during the chase (labeling with either [$^{35}$S]methionine or [$^{3}$H] leucine), implying either rapid destruction of intermediates or a highly processive mode of proteolysis. Because of the low abundance of α2 in α cells, a pulse-chase experiment in FIG. 12B, c was done using cells that carried MATα on a high copy plasmid. However, the rapid degradation of α2 was not due to its overproduction (by analogy, for example, to the metabolic instability of ribosomal proteins synthesized in stoichiometric excess (Maicas, E. et al., *Mol. Cell Biol.* 8:169-175 (1988); Tsay, Y-F., et al., *Genes Dev.* 2:664-676 (1988)) insofar as the half-life of α2 expressed from a single chromosomal copy of MATα was ~4 minutes at 30° C., close to the $t_{\frac{1}{2}}$ value above. Another implication of this result is that the pathway(s) responsible for α2 degradation operates well below saturation at normal cellular levels of the repressor.

Each of the Two Domains of α2 Contains a Degradation Signal

Figure 13A:
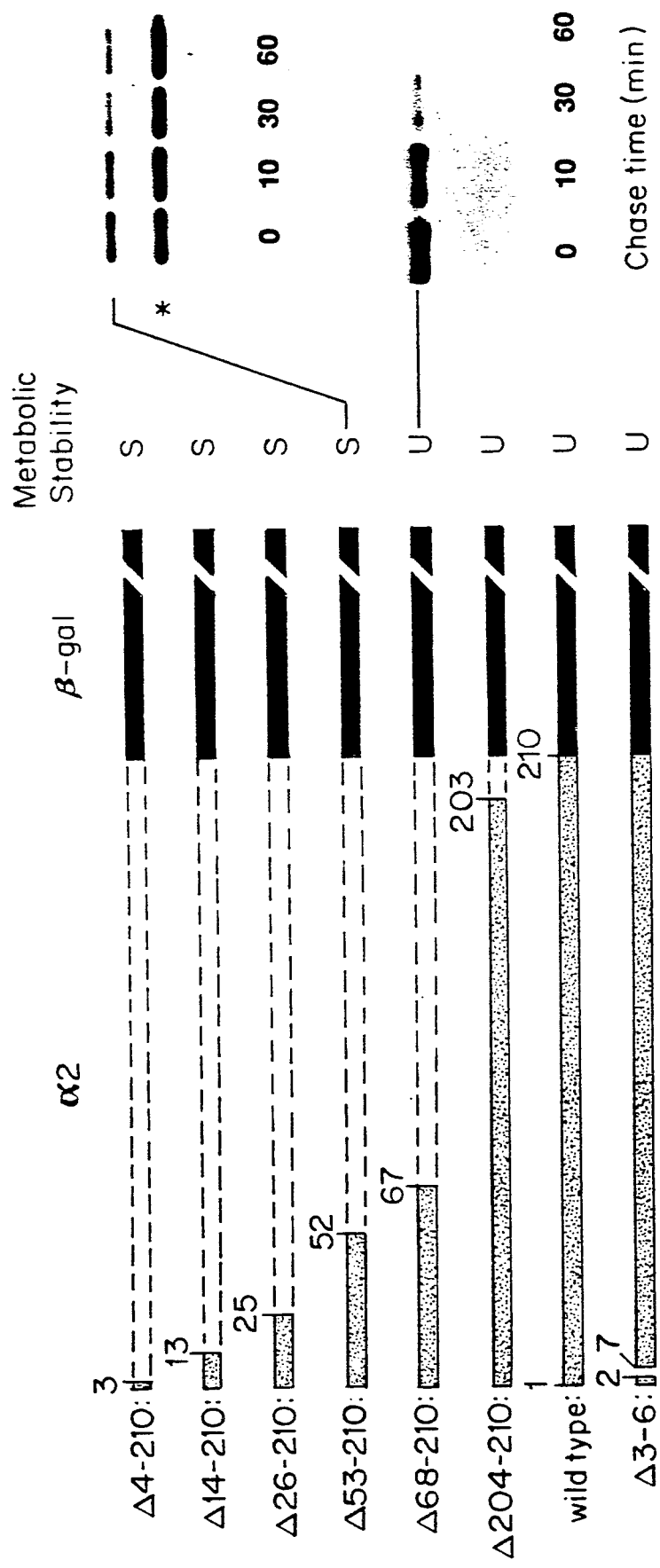
FIGS. 13A and B are diagrams illustrating the results of deletion analysis of degradation signals in $\alpha$2-$\beta$gal.
Figure 13B:
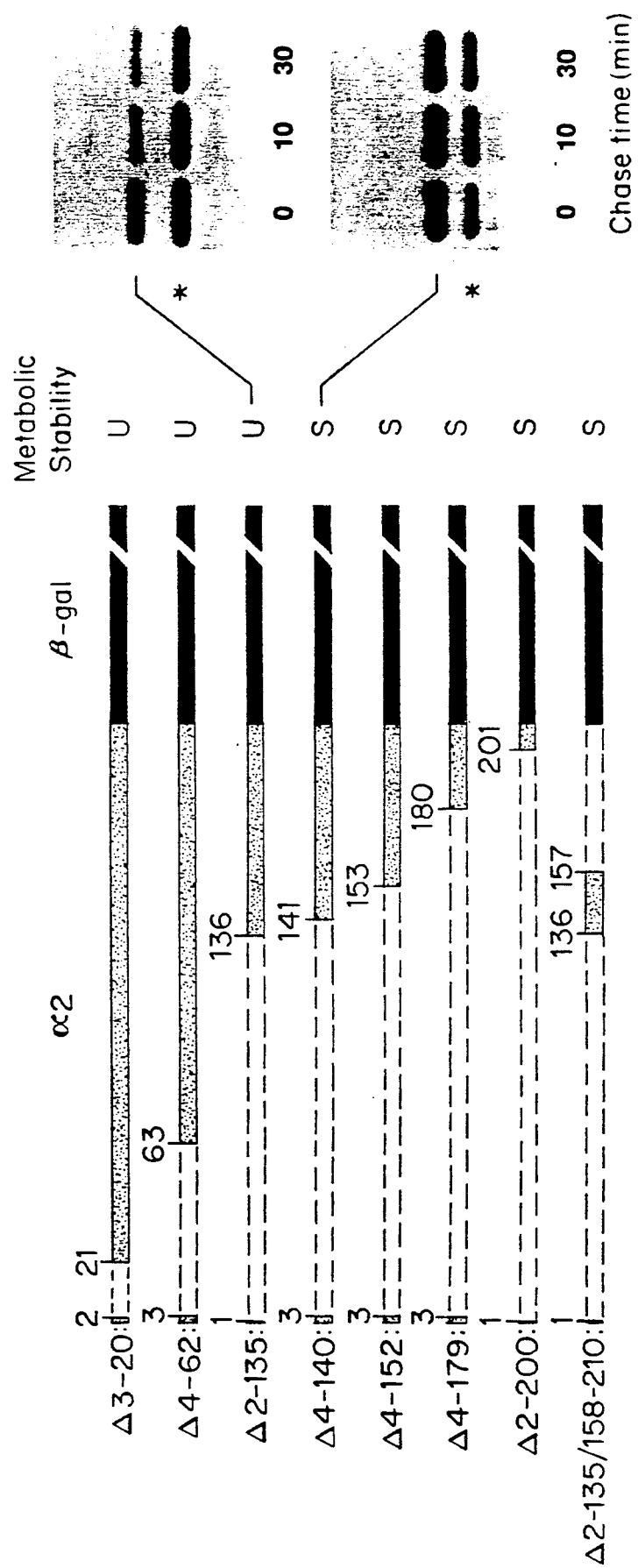

The metabolic instability of α2 could be a consequence of either some global property of the protein, such as low conformational stability (Parsell, D. A. and R. T. Sauer, *J. Biol. Chem.* 264:7590-7595 (1989)), or a more localized structural feature. The latter would be analogous to the signal sequences that target proteins to distinct subcellular compartments (Dingwall, C. and R. A. Laskey, *Ann. Rev. Cell Biol.* 2:367-390 (1986); Colman, A. and C. Robinson, *Cell* 46:321-322 (1986); Warren, G., *Nature* 327:17-18 (1987)). A search for degradation signals in α2 was conducted by examining a set of α2-βgal fusions with deletions in the α2 moiety (FIGS. 13A and B). Two series of deletion derivatives of α2-βgal, initiating either of the amino terminus of α2 or at the carboxyl terminus (the junction between the α2 and βgal sequences) were expressed in *S. cerevisiae*, and the rates of in vivo degradation were determined. All constructs share the same wild-type coding sequences of the *E. coli* βgal gene (lacZ), subcloned from pMC1871. Metabolically stable (S) and unstable (U) proteins are operationally defined as having initial in vivo half lives of more than ~3 hours (little or no detectable degradation during the chase period) and less than ~20 minutes, respectively.

Over two-thirds of the carboxyl-terminal region of the 210-residue α2 moiety could be deleted without significantly altering the rate of degradation of the fusion protein. FIGS. 13A and B shows two series of deletion derivatives of α2-βgal, initiating at either the amino or the carboxyl terminus of α2 (the junction between the α2 and βgal sequences) that were expressed in *S. cerevisiae*, and rates of in vivo degradation. For instance, Δ68-210, which contains only the first 67 residues of α2, was about as short-lived ("t₁" of ~10 minutes) as the full-length α2-βgal protein. However, deleting 15 additional residues toward the amino terminus (Δ53-210) yielded a long-lived α2-βgal derivative (FIGS. 13A and B). Deletions extending further toward the amino terminus also resulted in metabolically stable proteins. It was concluded that the amino-terminal region of α2 carries a degradation signal capable of targeting a normally long-lived protein such as βgal for rapid degradation in vivo, and an essential component of this signal lies within residues 53-67 of the repressor. Genetic evidence (see below) indicated that this degradation signal, uncovered using α2-βgal fusions, is also relevant to the degradation of the intact (unfused) α2.

Remarkably, an entirely different region of α2 also can function as a degradation signal. When nearly two-thirds of the amino-terminal region of the α2 sequence was deleted, the α2-βgal derivative obtained, Δ2-135, was approximately as short-lived ("t₁" of ~15 minutes) as the full-length α2-βgal (FIGS. 13A and B). As with the carboxyl-terminal deletions, a sharp transition between metabolically unstable and stable α2-βgal derivatives was also observed: removing just 5 more residues beyond residue 135 yielded a long-lived protein (Δ4-140, FIGS. 13A and B). Thus, the carboxyl-terminal 75-residue region of α2 can confer metabolic instability on an otherwise long-lived protein, and information within residues 136-140 is essential for this property.

As a prelude to a more detailed dissection of the carboxyl-terminal degradation signal in α2, we deleted residues 158-110 from the short-lived Δ2-135 protein. The derivative obtained, Δ2-13/158-210, was metabolically stable (FIGS. 13A and B). Therefore, information both downstream of residue 157 and upstream of residue 141 is required for the degradation signal to function.

The two independent degradation signals uncovered in the α2 repressor by the above analysis reside in its amino-terminal and carboxyl-terminal regions, respectively. These same regions have previously been shown to exist as structurally and functionally distinct globular domains in the repressor (Hall, M. N. and A. D. Johnson, *Science* 237:1007-1012 (1987); Sauer, R. T. et al., *Genes Dev.* 2:807-816 (1988)). Moreover, as shown below, the two degradation signals in α2 operate via genetically distinguishable pathways.

Isolation of Mutants Defective in α2 Degradation

The half-life of α2 remained unchanged in *S. cerevisiae* mutants defective in either vacuolar (lysosomal) proteolysis or the N-end rule pathway. Therefore, a genetic screen was devised for mutants impaired in α2 degradation. Since the intracellular level of α2-βgal is a function of its half-life, a plate assay with the chromogenic βgal substrate X-Gal should allow the detection of mutants in which α2-βgal is metabolically stabilized. The actual screen utilized the short-lived Δ68-210 protein (FIGS. 13A and B), which carries the amino-terminal but not the carboxyl-terminal degradation signal of α2. In addition to bypassing potential complications caused by the presence of both signals in the full-length protein, the use of Δ68-210 also avoided formation of the relatively long-lived, βgal-containing cleavage product that occurs with the full-length α2-βgal. Presence of this product would have greatly reduced the sensitivity of the screen to changes in the steady state level of α2-βgal.

To date, 20 mutants in which the Δ68-210 protein was metabolically stabilized have been obtained from a screen of ~40,000 survivors of ethyl methanesulfonate (EMS) mutagenesis (Experimental Procedures). The corresponding mutations involved at least 4 complementation groups. Pulse-chase experiments with representative alleles of two of the doa (degradation of alpha) mutants, doa1 and doa2, were conducted. The metabolic stability of Δ68-210 was greatly increased in these mutants, with little or no degradation detectable over one hour of chase, in contrast to the wild type "t₁" of ~10 minutes (FIGS. 13A and B and 14A to C).

Figure 14A:
FIGS. 14A to C are diagrams illustrating the isolation of S. cerevisiae mutants defective in $\alpha$2 degradation.
Figure 14B:
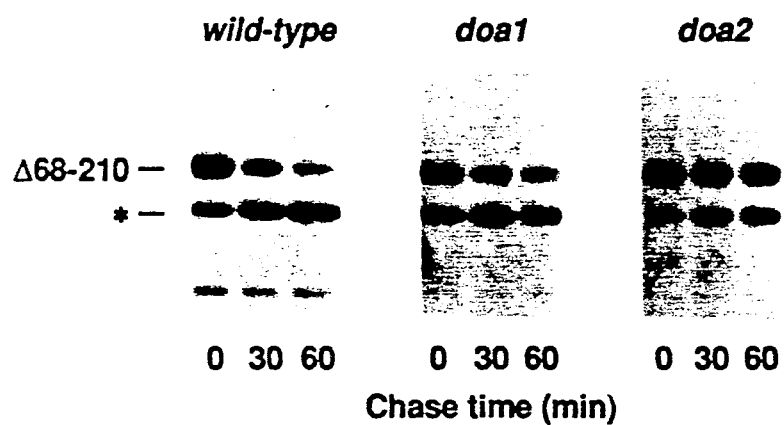
Figure 14C:
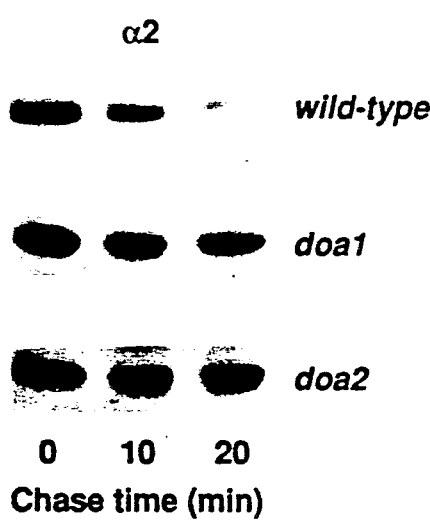
Figure 16A:
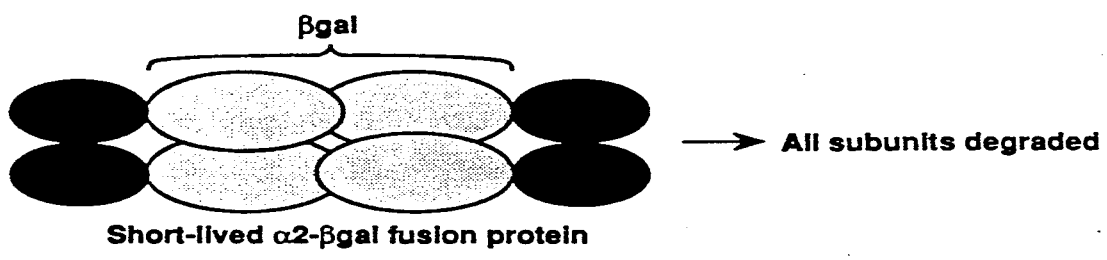
FIGS. 16A to D are diagrams illustrating the design of in vivo subunit mixing experiments.
Figure 16B:
Figure 16C:
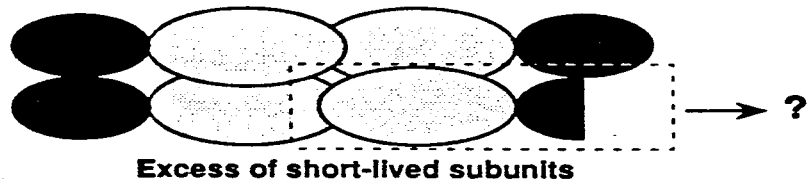
Figure 16D:
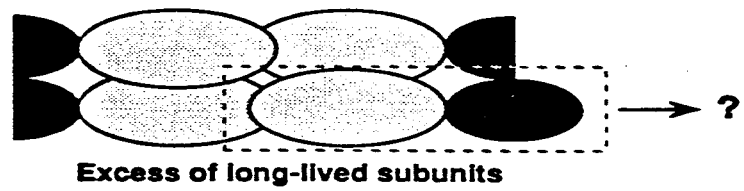

FIG. 14A summarizes the genetic screen for mutants defective in degrading the Δ68-210 derivative of α2-βgal that carries one, but not both of the α2 degradation signals. FIG. 14B shows results of pulse-chase analysis of the Δ68-210 protein in wild-type cells and in doa mutants at 36° C. FIG. 14C shows results from tests measuring the ability of various strains to degrade the intact (not fused to βgal) α2 repressor at 36° C.

The doa mutants were then examined for their ability to degrade the intact (unfused) α2 repressor (FIG. 14C). In every case tested (5 mutants representing at least 3 complementation groups), the metabolic stability of α2 was enhanced, with half-life increases relative to wild type of between 2- and 7-fold. It was concluded that the amino-terminal degradation signal in α2 identified through the analysis of α2-βgal fusions operates in the bona fide repressor as well. These results validate both the use of α2-βgal fusions to locate putative degradation signals in α2 and the use of a βgal-based screen to isolate mutants in α2 degradation.

While a detailed description of the doa mutants is beyond the scope of this application, we note that, in tetrad analyses, a number of additional phenotypes cosegregated with the α2 degradation defect (see Experimental Procedures). Some of the doa mutants were unable to sporulate as homozygous doa/doa diploids. Growth of at least two of the mutants was temperature-sensitive, and several of them had reduced growth rates at normal temperatures (23°-30° C.). Inasmuch as these pleiotropic effects are unlikely to be due to metabolic stabilization of α2 as such (Nasmyth, K. and D. Shore, *Science* 237:1162-1170 (1987); Herskowitz, I., *Microbiol. Rev.* 52:536-553 (1988)), they indicate that the pathways which degrade α2 have multiple functions in yeast. These functions presumably include the degradation of other proteins whose rapid turnover is physiologically essential.

The Two Degradation Signals in α2 Operate via Distinct Pathways

The Δ2-135 derivative of α2-βgal, which carries only the carboxyl-terminal degradation signal of α2 (FIGS. 13A and B), was introduced into three of the doa mutants identified through their defects in the degradation of an α2-βgal derivative containing only the amino-terminal signal. The Δ2-135 protein continued to be degraded at wild-type rates in the mutants (FIG. 15A). It was concluded that the two degradation signals detectable in α2 using the α2-βgal approach operates via genetically distinguishable pathways. As discussed above (FIGS. 14A to C), the amino-terminal degradation signal is active not only within a α2-βgal but within the intact (unfused) α2 repressor as well. Whether the carboxyl-terminal signal actually contributes to the metabolic instability of intact α2 remains to be determined. This uncertainty, however, does not influence the conclusion about the mechanistic difference between the amino- and carboxyl-terminal degradation signals in α2. Independent evidence for this conclusion is presented below.

Degradation of a Multisubunit Protein is Subunit-Specific

Recent work has shown that the α2 homodimer, while capable of selective binding to the operators of a cell-specific genes, is by itself insufficient for their transcriptional repression (Hall, M. N. and A. D. Johnson, Science 237:1007-1012 (1987)). A second protein, MCM1 (GRM, PRTF), is also required (Keleher, C. A. et al., Cell 53:927-936 (1988); Passmore, S. et al., Genes Dev., 3:921-935 (1989); Jarvis E. E. et al., Genes Dev. 3:936-945 (1989)). An α2 dimer and an MCM1 dimer apparently form a tetrameric repressor that turns off transcription of a cell-specific genes. MCM1 is present in all three cell types of S. cerevisiae and forms complexes with several different regulatory proteins. Thus, MCM1 is likely to be a more abundant and more metabolically stable protein than α2. This raises the question of whether the fate of MCM1 in a tetrameric complex with the short-lived α2 protein is different from that of α2 itself. More generally, it could be asked whether the mechanisms of in vivo protein degradation are such that an oligomeric protein can contain both long-lived and short-lived subunits. The design of in vivo "subunit mixing" experiments that address this question is shown in FIGS. 16A to D.

As described above, the initial α2-βgal fusion and some of its deletion variants exist in vivo as extremely short-lived homotetramers (FIGS. 13A and B and 16A), while other homotetrameric derivatives of α2-βgal are metabolically stable (FIGS. 13A and B and 16B). What would be the metabolic fate of individual subunits within an α2-βgal heterotetramer in which a majority of subunits is either of a short-lived or a long-lived type (FIG. 16C, D)? For example, if an α2-βgal subunit that is long-lived within a homotetramer (FIG. 16B) is present instead within a heterotetramer containing an excess of short-lived α2-βgal derivatives (FIG. 16C), will the long-lived subunit remain long-lived? In other words, it was asked whether the in vivo degradation machinery can distinguish those subunits of an oligomeric protein that carry a degradation signal from those that do not, or whether an entire oligomer is targeted for destruction even if only a subset of its subunits carry degradation signals.

Figures 17A, 17B, 17C:
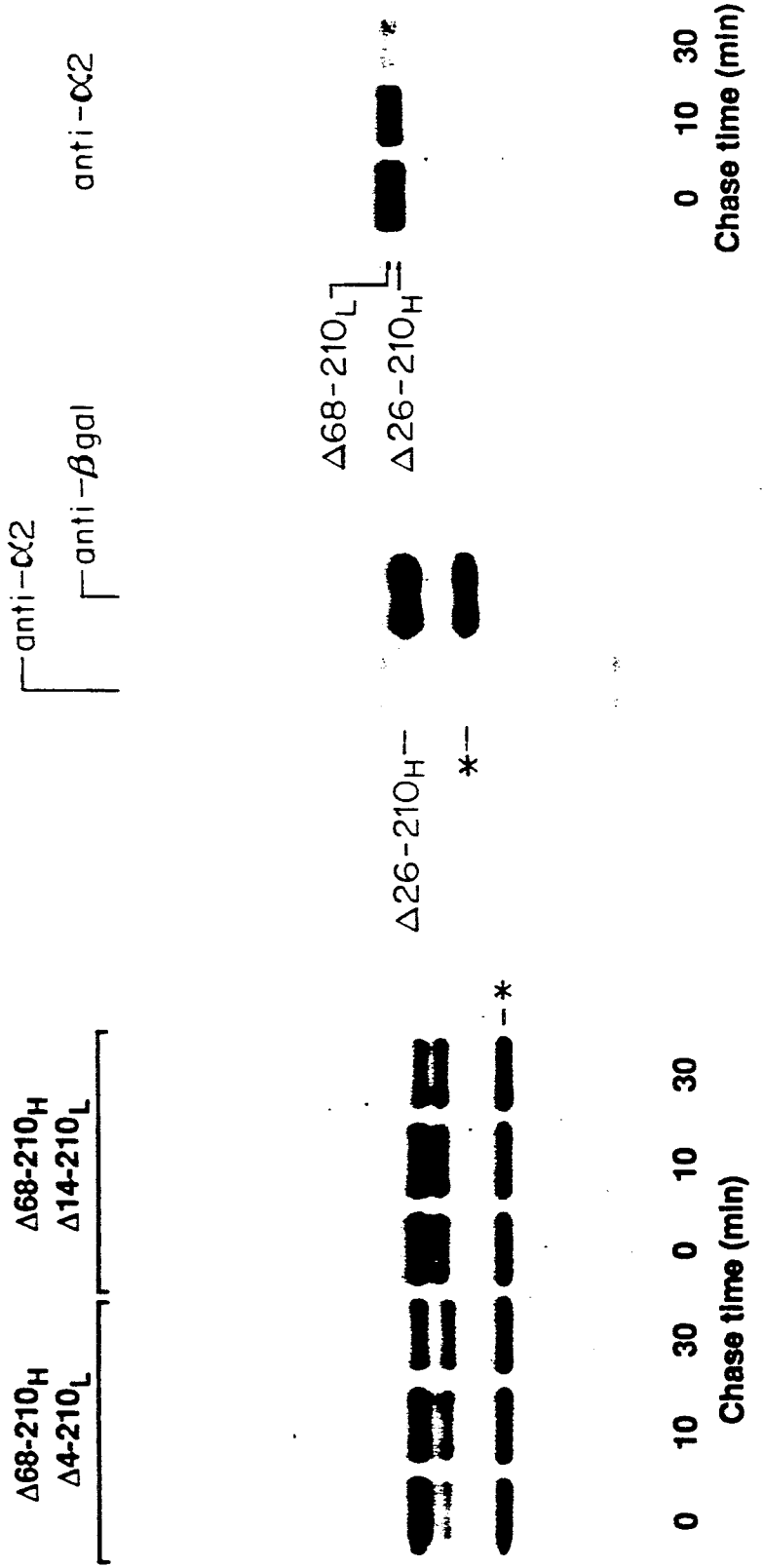
FIGS. 17A to C are diagrams illustrating that the degradation of an oligomeric protein is subunit-specific.

Mixed tetramers with biased subunit ratios were formed in vivo by expressing one of the α2-βgal subunits from a high copy plasmid and the other from a low copy plasmid in the same cell (Hall, M. N. et al., Cell 36:1057-1065 (1984); Hall, M. N. and A. D. Johnson, Science 237:1007-1012 (1987)). Because the short-lived (degradation signal-containing) α2-βgal subunits are larger than their long-lived counterparts (FIGS. 13A and B and 16A to D), they could be resolved by SDS-PAGE, allowing the metabolic stabilities of both species to be determined simultaneously. In two such experiments, in which an excess of the degradation signal-containing Δ68-210 subunit was coexpressed with either the long-lived Δ4-210 or Δ14-210 subunits, the subunits that were long-lived in a homotetramer remained long-lived even within a heterotetramer containing an excess of subunits that carried the amino-terminal degradation signal of α2 (FIG. 17A). An alternative interpretation of this result (FIG. 17A) is that in cells coexpressing both types of α2-βgal subunits, homotetramers might have formed in strong preference to heterotetramers. Another possibility is that long-lived subunits such as Δ14-210 could have inhibited the degradation of otherwise short-lived subunits such as Δ68-210 when present within the same heterotetramer.

Control experiments demonstrated that the results described above could not have resulted from lack of heterotetramer formation in vivo. These control experiments were made possible by the fact that the affinity-purified antibody to α2 (see Experimental Procedures) does not precipitate α2-βgal fusions with fewer than 26 amino-terminal residues of the α2 moiety. For instance, the Δ26-210 protein (FIGS. 13A and B), was precipitated by the antibody to βgal but was not precipitated from the same extract by the antibody to α2 (FIG. 17B). In contrast, when cells coexpressed Δ26-210 (from a high copy plasmid) and Δ68-210 (from a low copy plasmid), the Δ26-210 subunit could be precipitated by either anti-βgal or anti-α2 (FIG. 17C). Thus, Δ26-210/Δ68-210 heterotetramers actually did form in vivo, allowing coprecipitation of Δ26-210 by the antibody to α2. Such coprecipitation was also obtained with Δ14-210 substituted for Δ26-210 and was abolished by pretreatment of the samples with SDS.

When anti-α2 was used for immunoprecipitation, the Δ26-210 subunit was found to disappear along with Δ68-210 during the chase (FIG. 17C). In contrast, when anti-βgal was used, the same experiment showed that Δ26-210 did not become short-lived in the presence of an excess of the degradation signal-bearing Δ68-210 subunit (FIGS. 17A to C). The apparent disappearance of Δ26-210 during the chase (FIG. 17C) must therefore have been due to the degradation of Δ68-210 present in mixed tetramers with Δ26-210, the latter subunit being precipitable with anti-α2 only via the Δ68-210 subunit within the same heterotetramer. Thus, subunits lacking the amino-terminal degradation signal did not inhibit the destruction of the signal-bearing subunits, even when the latter were outnumbered within the heterotetramer. We conclude that the in vivo degradation of a multisubunit protein such as α2-βgal is subunit-specific, i.e., that an oligomeric protein can contain both long-lived and short-lived subunits.

Inhibition of the Carboxyl-Terminal Degradation Signal of α2 in Heteromeric Protein Complexes A series of in vivo subunit mixing experiments analogous to those in FIG. 17A was performed using Δ2-135, an α2-βgal derivative carrying only the carboxyl-terminal degradation signal (FIGS. 13A and B and 15B, C). As with the amino-terminal signal (FIG. 17A), overexpression of Δ2-135 was found not to affect the long half-life of the coexpressed Δ26-210 subunit that lacks a degradation signal (FIGS. 13A and B and 15B). Control experiments analogous to those with the amino-terminal degradation signal, using the antibody to α2, confirmed the formation of mixed tetramers in cells coexpressing Δ2-135 and Δ26-210. Interestingly, however, overexpression of Δ26-210 was found to inhibit degradation of the carboxyl-terminal signal-bearing Δ2-135 subunits expressed in the same cells (FIG. 15C). This effect is unlikely to be due to a steric shielding of the carboxyl-terminal degradation signal in (Δ2-135)-containing heterotetramers, since long-lived deletion derivatives of α2-βgal bearing only short segments from either end of the α2 moiety caused the same trans inactivation of the degradation signal. It is, therefore, probable that, unlike the amino-terminal degradation signal, the carboxyl-terminal signal of α2 is inactive when present in only a single subunit within an oligomeric assembly. The $D_2$ symmetry of the tetrameric βgal moiety (Langley, K. E. et al., *Proc. Natl. Acad. Sci. USA* 72:1254–1257 (1975); Kania, J. and D. T. Brown, *Proc. Natl. Acad. Sci. USA* 73:3529–3533 (1976)) and the dimeric nature of the α2 repressor (Hall, M. N. and A. D. Johnson, *Science* 237:1007–1012 (1987); Sauer, R. T. et al., *Genes Dev.* 2:807–816 (1988)) lead to the suggestion that a dimeric state of the carboxyl-terminal domain of α2 is required for the activity of its degradation signal. The subunit-autonomous nature of the amino-terminal degradation signal in α2 and the lack of this property in the carboxyl-terminal degradation signal support the genetic evidence that these two signals are mechanistically distinct.

Experimental Procedures

Yeast Strains

*S. cerevisiae* strains used in this study were DBY1705 (MATαleu2-3,112 ura3-52 lys2-801 gal2), DBY1826 (MATαleu2-3, 112 ura3-52 trpl his3-≠200 ade2-101), and HR125-5Dalf(Δ(MAT)::CAN1-14 leu2-3, 112 ura3-52 trpl his3 his4) (Hall, M. M. and A. D. Johnson, *Science* 237:1007–1012 (1987)).

Plasmid Constructions

Expression vectors pKKα2-lacZ and pKKα2 for producing α2-βgal and α2 in *E. coli* were constructed as follows. A BamHI-HindIII fragment of the *E. coli* expression vector pKK233-2 carrying the Ptrc promoter (Amann, E. and J. Brosius, *Gene* 40:183–190 (1985)), was ligated to a HindIII-SacI fragment of M13mp19 carrying α2-lacZ'. A 38-mer synthetic oligodeoxynucleotide was hybridized to the single-stranded DNA of the resulting M13mp19 phage derivative, causing the intervening sequence between Ptrc and the start codon of α2 to loop out. After filling in the gapped duplex and transforming into *E. coli* BMH71-18mutS (Kramer, W. et al., *Nucl. Acids Res.* 12:9441–9456 (1984)), phage DNAs were screened for the desired deletion by agarose gel electrophoresis. The (Ptrc-α2-lacZ')-containing SalI-SacI fragment was then ligated to a SAlI-SACi vector fragment of pKK233-2 that carried the region of lacZ 3' to the SacI site. The resulting pKKα2-lacZ vector produced a αgal fusion protein of the expected size in *E. coli* JM101 upon induction with IPTG. The presence of the correct α2 moiety was confirmed by amino-terminal microsequencing (see below) of the purified fusion protein. The pKKα2 expression vector was produced from pKKα2-lacZ by ligating its BamHI-XbaI fragment carrying the Ptrc promoter and ~75% of the α2 coding region to a PUC19-based XbaI-XhoI fragment of the αX152 derivative of MATα (Tachell, K. et al., *Cell* 27:25–35 (1981)), carrying the rest of the α2 reading frame. The resulting fragment was then ligated to the larger BamHI-HindII fragment of pKK233-2, yielding pKKα2.

The Δ53-210 α2-βgal derivative (FIGS. 13A and B) was constructed by subcloning a ~3 kb SalI fragment of pMC1871 (Casadaban, M. J. et al., *Meth. Enzymol.* 100:293–308 (1983)) that encodes *E. coli* μgal into the XhoI linker site of matα2::αX182 carried in the plasmid YRp7 (Tatchell, K. et al., *Cell* 27:25–35 (1981)). The resulting Δ53-210 construct encoded a fusion of the first 52 residues of α2 to βgal. The HindIII fragment containing Δ53-210 was then subcloned into both high copy (YEp13) and low copy (YCp50) plasmids (Parent, S. A. et al., *Yeast* 1:83–138 (1985)). Only the low copy plasmid encoding Δ53-210 yielded tranformants in *S. cerevisiae*. Hall et al. (*Cell* 36:1057–1065 (1984)) noted that the Δ14-210 and Δ26-210 proteins (FIGS. 13A and B) were lethal if expressed from the MATα2 promoter in high copy plasmids in the HR125-5Dα strain. This effect was not observed in DBY1705, nor could we confirm, with our yeast strains, the previously reported (Hall, M. N. et al., *Cell* 36:1057–1065 (1984)) toxicity of Δ68-210 upon its expression from high copy plasmids. The Δ2-135/158-210 derivative (FIGS. 13A and B) was constructed as follows: Δ2-135 in YEp13 (Hall, M. N. and A. D. Johnson, *Science* 237:1007–1012 (1987)), was digested with XbaI, treated with exoVII, and then digested with HindIII. The resulting ~2 kb fragment encoding the amino terminus of α2 from Δ2-135 was ligated to the SmaI-SacI lacZ' fragment from pMC1871 and to the SacI-HindIII fragment of α2-135 encoding the carboxyl-terminal region of βgal. Nucleotide sequencing of the final plasmid construct (Kraft, R. et al., *Biotechniques* 6:544–546 (1988)), showed that it encoded the Δ2-135/158-210 protein (FIGS. 13A and B).

Pulse-chase Analysis

*S. cerevisiae* cells transformed (Ito, H. et al., *J. Bacteriol.* 153:163 (1983)) with plasmids of interest with grown at 30° C. in a minimal SD medium (Sherman, F. et al., *Methods in Yeast Genetics,* Cold Spring Harbor Laboratory, Cold Spring Harbor, N.Y. (1986) to an $A_{600}$ of approximately 1 (mid-exponential phase). Cells from a 10-ml culture were harvested by filtration on a Millipore microtiter filtration plate, washed several times with methionine-free SD medium, resuspended in 0.3 ml of 0.5% glucose, 40 mM potassium phosphate (pH 7.4), and labeled for 5 minutes at 30° C. (unless stated otherwise) with 0.15 mCi of $^{35}$S-Translabel (ICN; ~80% [$^{35}$S]methionine, ~20% [$^{35}$S]cysteine). Labeled cells were collected by filtration and resuspended in SD medium supplemented with 10 mM L-methionine, 0.2 mg/mll cycloheximide, and 50 μg/ml trichodermin (a gift from Leo Pharmaceutical Products, Ballerup, Denmark). (In some experiments, translation inhibitors were omitted; a slight increase in labeling during the case was observed, resulting in a less than 10% apparent increase in half-life values (data not shown).) Samples (0.1 ml) were withdrawn at indicated times and mixed with 0.8 ml of cold buffer A (1% Triton X-100, 0.15M NaCl, 5 mM Na-EDTA, 50 mM Na-HEPES, pH 7.5) containing leupeptin, pepstatin A, chymostatin, antipain and aprotinin (Sigma) (each at 20 μg/ml), in addition to 0.4 ml of 0.5 mm glass beads. Unless indicated otherwise, cells were disrupted by vortexing 3 times for 1 minute intervals at 4° C.; the extracts were centrifuged at 12,000 g for 10 minutes. (An alternative lysis procedure was used in some experiments as indicated in the figure legends. Aliquots of cell suspension were mixed with an equal volume of 2% SDS, 30 mM dithiothreitol, 90 mM Na-HEPES, pH 7.5 and incubated at 100° C. for 3 minutes. The extracts were diluted 10-fold with buffer A plus protease inhibitors, and centrifuged as above.) Acid-insoluble $^{35}$S in the supernatants was determined, and samples containing equal amounts of acid-insoluble $^{35}$S were immunoprecipitated with a molar excess of either an affinity-purified antibody of α2 (see below) or a monoclonal antibody of βgal (a gift from J. Partaledis and T. Mason, University of Massachusetts, Amherst), obtained via J. Paul and R. Hynes (M.I.T.); see Bachmair, A. et al., *Science* 234:179-186 (1986)). After incubation at 4° C. for ~2 hours, Protein A-agarose (Repligen or Pharmacia) was added, and the suspensions incubated with rocking at 4° C. for ~1 hour, followed by a 15-second, low speed centrifugation. The pellets were washed three times in buffer A containing 0.1% SDS, resuspended in electrophoresis sample buffer (Laemmli, U.K., *Nature* 227:680-685 (1970)), incubated at 100° C. for 3 minutes, centrifuged as above, and subjected to electrophoresis in 6% polyacrylamide-SDS gels, with subsequent fluorography.

Amino Acid Sequencing

Approximately 10$^{11}$ DBY1705 cells carrying a high copy, YEp13-based plasmid that expressed α2-βgal from the MATα2 promoter (Hall, M. N. et al., *Cell* 36:1057-1065 (1984)), were grown to late exponential phase in SD medium, and disrupted by the Triton/glass bead method.

The extract was centrifuged at 13,000 g for 1 hour at 4° C., and the supernatant was immunoprecipitated with antibody to βgal. The precipitated α2-βgal and its in vivo cleavage product was subjected to SDS-PAGE and electroblotted onto a PVDF filter (Millipore) Matsudaira, P., *J. Biol. Chem.* 262:10035-10038 (1987)). After briefly staining with Coomassie Blue, the α2-βgal cleavage product was excised and subjected to amino acid sequencing by Edman degradation for 6 cycles using an Applied Biosystems 470A Protein Sequencer equipped with an online 120A PTH Analyzer.

Antibody to α2 Protein

The α2-βgal protein was purified from isopropylthiogalactoside (IPTG)-induced *E. coli* carrying pKKα2-lacZ by subjecting an extract prepared as in Gonda et al., (*J. Biol. Chem.* 264:16700-16712 (1989)) to affinity chromatography on aminophenylthiopyranogalactoside-Sepharose (APTG-Sepharose) (Ullmann, A., *Gene* 29:27-31 (1984)). The affinity-purified α2-βgal was purified further by electrophoresis in a preparative-scale 6% polyacrylamide-SDS gel. The α2-βgal band was excised, and macerated gel slices, suspended in Freund's complete adjuvant, were injected subcutaneously into female New Zealand white rabbits (either 0.1 or 0.2 mg of α2-βgal per rabbit) (Carroll, S. B. and A. Laughton, *DNA Cloning: A Practical Approach*, D. M. Glover, ed. (IRL Press, Oxford), pp. 89-111, 1987). The antiserum to α2-βgal was precipitated with 18% (w/v) Na$_2$SO$_4$, yielding an IGg-enriched fraction. The first affinity column contained *E. coli* βgal (Sigma) bound to CNBr-activated Sepharose; the second column contained α2-βgal crosslinked with dimethylpimelimidate (Pierce) to anti-βgal-Sepharose (the latter was made using the eluate of the first column). The flow-through from the first column was applied to the second one, and the bound fraction was eluted with 4M guanidine hydrochloride. The eluate was dialyzed against 0.15% NaCl, 10 mM K$_2$HPO$_4$ (pH 7.2) at 4° C. and passed through the β-gal-Sepharose column to remove any residual antibodies to βgal. The affinity-purified anti-α2 was concentrated in Centriprep tubes (Amicon), made 40% (v/v) in glycerol, and stored at either −20° C. or −85° C. Immunoprecipitation with this antibody of extracts from [$^{35}$S]methionine-labeled *S. cerevisiae* yielded, upon SDS-PAGE, a single band of predicted molecular mass with α but not a cells (FIG. 1D). Furthermore, electrophoretic bands of the expected molecular mass were seen by immunoblot analyses of extracts from *E. coli* expressing either α2 or α2-βgal but not in control extracts. The anti-α2 also precipitated the same α2-βgal derivatives that were detectable using antibody to βgal, provided the derivative retained the requisite epitope(s) of α2 (FIGS. 13A and B).

Isolation of DOA Mutants

DBY1705 cells carrying Δ68-210 (FIGS. 3A to C) in the low copy YCp50 vector (Hall, M. N. et al., *Cell* 36:1057-1065 (1984)) were grown to stationary phase in minimal medium, mutagenized with EMS to ~20% survival, and spread onto minimal plates (~40,000 survivors). Cells were then replica-plated to plates containing the chromogenic βgal substrate X-Gal (Rose, M. et al., *Proc. Natl. Acad. Sci. USA* 78:2460-2464 (1981)) and incubated at 23° C. for 3 days, and then at 36° C. for 3 days. Colonies that turned blue at either 23° C. or 36° C. (wild-type colonies are white) were picked and re-screened by dispersing cells in water in 96-well microtiter plates and stamping cells onto fresh X-Gal indicator plates. Strains that passed the rescreening test were grown in liquid cultures and quantitatively assayed for βgal activity using ortho-nitrophenyl galactoside (ONPG) as substrate. Sixty potential mutants (with βgal activity levels at least 3-fold higher than wild-type) were isolated. Pulse-chase analyses of these mutants identified 25 strains that showed a significant (at least 2-fold) increase in the "t$_1$" of the Δ68-210 fusion protein. Immunofluorescence analysis indicated that, in all of these doa (Degradation Of Alpha) mutants, the Δ68-210 protein was concentrated in the nucleus.

These strains were streaked onto 5-fluoro-orotic acid plates (Boeke, J. D. et al., *Mol. Gen. Genet.* 197:345-346 (1984)) to isolate colonies from which the Δ68-210 bearing plasmid had been lost. Cells from these colonies were then retransformed with the wild-type YCp50::Δ68-210 plasmid. Assays for βgal activity in both plate and liquid cultures reduced to 20 the number of strains that continued to show higher than wild-type levels of Δ68-210, indicating that the corresponding mutations were chromosomal and not plasmid-linked.

The plasmid-cured doa mutants were backcrossed to MHY101, a strain derived from DBY1826 by integrating the Δ68-210 fusion construct into the LEU 2 locus, using the YIp33 vector (Parent, S. A. et al., *Yeast* 1:83-138 (1985)); Orr-Weaver, T. L. et al., *Proc. Natl. Acad. Sci. USA* 78:6354-6358 (1981)). The site of integration was verified by Southern hybridization analysis and allelism tests. Segregants from sporulated diploids carrying both the integrated reporter gene encoding Δ68-210 and the doa degradation defect were then identified. The segregants were used for subsequent backcrossing, complementation, and segregation analyses. Complementation tests between different doa mutants were done on X-Gal plates. In ambiguous cases, tetrad analysis was used to test the segregation pattern of each pair of mutations. Backcrosses between doa mutants and MHY101, followed by sporulation and tetrad dissections, allowed tests of cosegregation of the α2 degradation defect with other mutant phenotypes, such as inability to sporulate.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method for metabolically destabilizing a protein or peptide of interest in a eukaryotic cell, the protein or peptide of interest containing a second determinant for the N-end rule of protein degradation, the method comprising transforming the cell with an expressible DNA construct comprising a DNA sequence encoding ubiquitin fused in frame with and immediately five-prime to a DNA sequence encoding a targeting protein or peptide having a destabilizing amino acid residue according to the N-end rule of protein degradation immediately following ubiquitin, but lacking a second determinant of the N-end rule-based degradation signal, wherein the protein or peptide of interest and the targeting peptide or protein are subunits or portions of subunits of a single oligomeric protein and wherein association of the targeting peptide with the peptide or protein of interest results in destabilization of the protein or peptide of interest.

2. A method of claim 1 wherein the eukaryotic cell is a yeast cell.

3. A method of claim 2 wherein the destabilizing amino acid residue is selected from the group consisting of Ile, Glu, Hihs, Tyr, Gln, Phe, Leu, Asp, Asn, Lys, Arg and Trp.

4. A method of claim 1 wherein the single oligomeric protein is a homomeric protein.

5. A method of claim 1 wherein the single oligomeric protein is a heteromeric protein.

6. A recombinant DNA molecule comprising a DNA sequence encoding ubiquitin fused in frame to a DNA sequence encoding a targeting peptide or protein which interacts specifically with a protein or peptide of interest, the targeting peptide or protein lacking a second determinant of the N-end rule-based degradation signal, and having a destabilizing amino-terminal amino acid residue according to the N-end rule of protein degradation, wherein the protein or peptide of interest and the targeting peptide or protein are subunits of a single oligomeric protein.

* * * * *